(12) United States Patent
Smith et al.

(10) Patent No.: US 9,177,106 B2
(45) Date of Patent: Nov. 3, 2015

(54) SYSTEM AND METHOD FOR DATA COLLECTION AND MANAGEMENT

(75) Inventors: Kyle B. Smith, San Pablo, CA (US); Richard E. Shaw, Burlingame, CA (US)

(73) Assignee: Sutter Health, Sacramento, CA (US)

( * ) Notice: Subject to any disclaimer, the term of this patent is extended or adjusted under 35 U.S.C. 154(b) by 272 days.

(21) Appl. No.: 12/646,791

(22) Filed: Dec. 23, 2009

(65) Prior Publication Data

US 2010/0174558 A1 Jul. 8, 2010

Related U.S. Application Data

(63) Continuation of application No. PCT/US2008/008092, filed on Jun. 27, 2008.

(60) Provisional application No. 60/948,635, filed on Jul. 9, 2007.

(51) Int. Cl.

| | |
|---|---|
| *G06F 19/00* | (2011.01) |
| *G06Q 10/00* | (2012.01) |
| *G06Q 50/22* | (2012.01) |
| *G06Q 50/24* | (2012.01) |

(52) U.S. Cl.
CPC .............. *G06F 19/322* (2013.01); *G06Q 10/00* (2013.01); *G06Q 50/22* (2013.01); *G06Q 50/24* (2013.01)

(58) Field of Classification Search
CPC ....... G06Q 50/22; G06Q 50/24; G06Q 10/00; G06Q 10/10; G06Q 10/0637
See application file for complete search history.

(56) References Cited

U.S. PATENT DOCUMENTS

| | | | |
|---|---|---|---|
| 5,772,585 | A | 6/1998 | Lavin et al. |
| 5,819,248 | A | 10/1998 | Kegan |

(Continued)

FOREIGN PATENT DOCUMENTS

| | | |
|---|---|---|
| AU | 775480 | 12/2004 |
| CA | 2398142 | 11/2011 |

(Continued)

OTHER PUBLICATIONS

International Search Report and Written Opinion of the International Searching Authority mailed Sep. 17, 2008 in Patent Cooperation Treaty Application No. PCT/US2008/008092, filed Jun. 27, 2008.

(Continued)

*Primary Examiner* — Michelle L Le
(74) *Attorney, Agent, or Firm* — Carr & Ferrell LLP

(57) ABSTRACT

Collecting, validating, managing, and sharing data, for example healthcare and patient data, may include using a networked portable device. A forms-based system and process (referred to in some embodiments as DirectForms™) may allow clinical staff to efficiently collect and validate data on portable devices. In accordance with an embodiment, the system combines a portable computing device, validation of data, network connectivity, and an opportunity for shared effort among users via industry-standard (for example HL7 compliant) or customized interfaces. A server-based utility may route forms and HL7-compliant data transaction exports. Interfaces may provide for merging data into appropriate patient records. Some systems may be used in an ambulatory care setting. Various aspects may provide for improved clinical assessment, effective patient management, cost savings, and the ability to provide a more efficient billing process.

20 Claims, 38 Drawing Sheets

(56) References Cited

U.S. PATENT DOCUMENTS

| | | | |
|---|---|---|---|
| 5,924,101 | A | 7/1999 | Bach et al. |
| 6,098,061 | A | 8/2000 | Gotoh et al. |
| 6,658,396 | B1 | 12/2003 | Tang et al. |
| 7,026,121 | B1 | 4/2006 | Wohlgemuth et al. |
| 7,181,017 | B1 | 2/2007 | Nagel et al. |
| 7,493,299 | B2 | 2/2009 | Entwistle |
| 2003/0037018 | A1 | 2/2003 | Entwistle |
| 2003/0233259 | A1* | 12/2003 | Mistretta et al. .......... 705/4 |
| 2005/0131738 | A1* | 6/2005 | Morris ..................... 705/2 |
| 2006/0047539 | A1 | 3/2006 | Huang |
| 2006/0111933 | A1 | 5/2006 | Wheeler |
| 2007/0021977 | A1 | 1/2007 | Elsholz |
| 2007/0022086 | A1 | 1/2007 | Elsholz |
| 2007/0033535 | A1 | 2/2007 | Cornacchia, III |
| 2007/0106537 | A1 | 5/2007 | Moore |
| 2009/0182699 | A1 | 7/2009 | Entwistle |

FOREIGN PATENT DOCUMENTS

| | | |
|---|---|---|
| GB | 2336008 | 10/1999 |
| JP | H11-219297 | 6/1999 |
| NZ | 520304 | 5/2004 |
| SG | 90651 | 12/2004 |
| WO | WO0157698 | 8/2001 |
| WO | WO2009008968 | 1/2009 |

OTHER PUBLICATIONS

Aggarwal, Charu C., "Hierarchical Subspace Sampling: A Unified Framework for High Dimensional Data Reduction, Selectivity Estimation and Nearest Neighbor Search", ACM SIGMOD 2002, Jun. 4-6, 2002, Madison, Wisconsin, pp. 452-463.

Orfali, Robert et al., "The Essential Distributed Objects Survival Guide", John Wiley and Sons, Inc., 1996.

Huo, Xiaoming, et al., "Support Vector Trees: Simultaneously Realizing the Principles of Maximal Margin and Maximal Purity", 2002 Technical Report, The logistics Institute, Georgia Tech and the Logistics Institute—Asia Pacific, national University of Singapore, 2002, pp. 1-19.

Bennett, Kristin P., "Enlarging the Margins in Perceptron Decision Trees", Machine Learning, 41, 2000, pp. 295-313.

Bichindaritz et al., "Case-Based Reasoning in Care-Partner: Gathering Evidence for Evidence-Based Medical Practice", 1998.

First Examination Report of the European Patent Office mailed May 11, 2010 in European Patent Convention Application No. 01908496. 1, filed Feb. 7, 2001.

Grosso et al. "Knowledge Modeling at the Millennium (The Design and Evolution of Protégé—2000)", Proceedings of the Knowledge Acquisition Workshop KAW 99, 1999, pp. 16-21. http://www.das.ufsc.br/~gb/pg-ia/Protege05/design.pdf.

Bergmann et al. "Similarity Measures for Object-Oriented Case Representations", LNCS-Proceedings of the 4th European Workshop on Advances in Case-Based Reasoning, vol. 1488, 1998, pp. 25-36.

Second Examination Report of the European Patent Office mailed Oct. 20, 2011 in European Patent Convention Application No. 01908496.1, filed Feb. 7, 2001.

Musen et al. "EON: A Component-Based Approach to Automation of Protocol-Directed Therapy", Journal of the American Medical Informatics Association, vol. 3, No. 6, 1996, pp. 367-388.

Office Action of the Canadian Intellectual Property Office mailed May 28, 2010 in Canadian Application No. 2398142, filed Feb. 7, 2001.

* cited by examiner

| FIG. 4A |
|---------|
| FIG. 4B |

NCDR-ACTION  Section Select ☐
Data Collection Form

Presentation Features — 172

Arrived at participating hospital: ☐ Yes ☐ No
Date ☐☐/☐☐/☐☐☐☐  🗓
Time ☐☐:☐☐  00:00 to 23:59  ☐ n/a Transfer from another hospital: ☐ Yes ☐ No
Arrival at outside hospital:
Date ☐☐/☐☐/☐☐☐☐  🗓
Time ☐☐:☐☐  00:00 to 23:59  ☐ n/a Transfer from outside hospital:
Date ☐☐/☐☐/☐☐☐☐  🗓
Time ☐☐:☐☐  00:00 to 23:59  ☐ n/a Patient transferred by EMS: ☐ Yes ☐ No
Arrival at outside hospital:
Date ☐☐/☐☐/☐☐☐☐  🗓
Time ☐☐:☐☐  00:00 to 23:59  ☐ n/a

---

Tabs — 170:
| Presentation Signs/Symp. Demo | Medical History Oral Medications | Oral Meds con't IV\Sub Meds | IV\Sub Meds cont'd In-Hosp Procs — 178 |

1st 12-lead ECG obtained: ☐ Yes ☐ No
Date ☐☐/☐☐/☐☐☐☐  🗓
Time ☐☐:☐☐  00:00 to 23:59  ☐ n/a If No, was first 12-lead ECG obtained pre-hospital:
☐ Yes  ☐ No ECG Findings:
☐ ST depression
☐ Transient ST elevation than 10 minutes
☐ T-wave inversion
☐ New LBBB
☐ Persistent ST elevation Location patient first evaluated:
☐ Emergency Department Transferred Date ☐☐/☐☐/☐☐☐☐  🗓
from ED:  Time ☐☐:☐☐  00:00 to 23:59  ☐ n/a
☐ ICU/CCU/Telemetry/Cardiac Floor
☐ Cath Lab
☐ Other or non-cardiac

FIG. 4B

Signs and Symptoms at Presentation

Onset date and time of ischemic symptoms: ☐/☐☐/☐☐☐☐ ☐☐:☐☐ 00:00 to 23:59
☐ n/a

Heart rate on admission: ☐☐☐ bpm

Signs of CHF: ☐ Yes ☐ No  If Yes, type ☐☐☐☐☐

Positive Cardiac Markers ☐ Yes ☐ No    Systolic blood pressure on admission: ☐☐☐ mmHg

174

Demographics

Age: ☐☐ years

Sex: ☐ Male ☐ Female

Weight: ☐☐☐ kg

Height: ☐☐☐.☐ cm

Race/ethnicity: ☐ White           ☐ American Indian/Alaskan Native
                ☐ Black/African   ☐ Native Hawaiian/Pacific Islander
                ☐ American        ☐ Other
                ☐ Asian Hispanic Origin:  ☐ Yes    ☐ No Insurance Status: ☐ HMO/private  ☐ Self/none
                  ☐ Medicare      ☐ Military/VAMC
                  ☐ Medicaid

176

In-Hosp Procs cont'd | In-Hosp Clin Events | Lab Results | Lab Results cont'd Discharge

180

Patient First Name: ☐☐☐☐☐☐☐☐☐☐☐☐☐☐☐☐☐☐☐
Patient Last Name:  ☐☐☐☐☐☐☐☐☐☐☐☐☐☐☐☐☐☐☐ ▲
MRN: ☐☐☐☐☐    Account Number ☐☐☐☐☐☐☐

HF CORE MEASURES

First Name ☐☐☐☐☐☐☐☐☐☐☐☐☐☐☐☐☐☐☐
Last Name ☐☐☐☐☐☐☐☐☐☐☐☐☐☐☐☐☐☐☐☐☐☐☐
MR #: ☐☐☐☐☐☐☐  Account # ☐☐☐☐☐☐☐☐☐
Admission Date 📅 ☐☐/☐☐/☐☐☐☐  Discharge Date 📅 ☐☐/☐☐/☐☐☐☐

*(184)* — Demographics / Concurrent Review

Concurrent Review Questions

| | | | |
|---|---|---|---|
| Comfort Measures Only | ☐Yes ☐No | Med Rec Form Initiated | ☐Yes ☐No |
| Concurrent Review | ☐Yes ☐No | Med Rec Form Completed | ☐Yes ☐No |
| CHF Care Plan | ☐Yes ☐No | D/C Summary Matches Form | ☐Yes ☐No |
| CHF Home Instruction Sheet | ☐Yes ☐No | CHF Readmit | |
| CHF Measure D/C Screen | ☐Yes ☐No | | |
| Core Measure Doc Initiated | ☐Yes ☐No | | |

*(186)* *(182)* — Core Measures

Discharge Nursing Unit [_____]

Check box for list
D/C Physician 1 ☐ ☐☐☐☐☐☐☐☐☐☐☐☐☐☐☐☐☐☐☐☐

Physician 1 Specialty ☐☐☐☐☐☐☐☐☐☐☐☐☐☐☐☐☐☐☐☐

D/C Physician 2 ☐ ☐☐☐☐☐☐☐☐☐☐☐☐☐☐☐☐☐☐☐☐

Physician 2 Specialty ☐☐☐☐☐☐☐☐☐☐☐☐☐☐☐☐☐☐☐☐

Comments

[ edit selection ]

| First Name | | Last Name | |
|---|---|---|---|
| Referring Cardiologist | | Surgeon Name | |
| Contact Name | Contact Telephone # | Relationship to patient | |

192A

| Admit Date | Surgery Date   Arrival Time   CABO#   Valve Replacements | | |
|---|---|---|---|
| Pre-Op History | Day of Surgery/ICU | PostOp Day #1 | PostOp Day #2 |
| | CV Rhythm<br>Status<br>Cl #   Neuro: | Rhythm<br>Status<br>Cl #   Neuro: | Rhythm<br>Status<br>Cl #   Neuro: |
| | Pulm<br><br>Ext   Sat   % | Ext   Sat   % | Ext   Sat   % |
| | Labs<br>Cr   INR | INR | INR |
| | DI&I<br>I&O<br>WT:         kg | kg | kg |
| | Activity<br>Dist          * | Dist          * | Dist          * |
| Cr   Ef:<br>Comments | Clin Variances | | |
| | Variances | | |
| | Incisions: Stemat: Leg: | Incisions: Stemat: Leg: | Incisions: Stemat: Leg: |

194A

196A

HOSPITAL STAY SUMMARY          Discharged to:
ET Time  Total/LOS:  ICU LOS:  SNF LOS:   ☐ SNF Home
                                          ☐ Home
☐☐-☐    ☐☐☐      ☐☐☐     ☐☐☐       ☐ Other

*FIG. 6A*

| Medical Record Number | Populate Demographics □ | SURGERY DAILY FLOWSHEET | |
|---|---|---|---|
| Date of Birth | Gender | | |
| Other | O# pump | POPULATE SURGERY SECTION □ | |

| PostOp Day #3 | PostOp Day #4 | PostOp Day #5 | PostOp Day #6 |
|---|---|---|---|
| Rhythm Status Cl # Neuro: | Rhythm Status Cl # Neuro: | Rhythm Status Cl # Neuro: | Rhythm Status Cl # Neuro: |
| Ext Sat % | Ext Sat % | Ext Sat % | Ext Sat % |
| INR ⋈ | INR ⋈ | INR ⋈ | INR ⋈ |
| kg | kg | kg | kg |
| Dist * | Dist * | Dist * | Dist * |
| | | | |
| | | | |
| Incisions: Sternat: Leg: | Incisions: Sternat: Leg: | Incisions: Sternat: Leg: | Incisions: Sternat: Leg: |
| Special Issues: | Phone followup:□Yes □No  Risk Score □□□ | | |
| | Advance Dis  □Yes □No  Pre-Op Ed □Yes □No | | |

*FIG. 6B*

| Carotid Stent Data |
|---|
| Page 1 – PATIENT DEMOGRAPHICS |

Medical Record #: ☐☐☐-☐☐-☐☐  S  R   SSN ☐☐☐-☐☐-☐☐☐☐

Patient's Last Name: ☐☐☐☐☐☐☐☐☐☐☐☐☐☐☐☐☐☐☐☐☐

Patient's First Name: ☐☐☐☐☐☐☐☐☐☐☐☐☐☐☐☐☐☐☐☐☐

Date of Birth: (MM/DD/YYYY) ☐☐/☐☐/☐☐☐☐

Gender: ☐ Male  ☐ Female   Race: ☐☐☐☐☐☐☐   ☐ Hispanic?

Primary Ins: [‾‾‾‾‾‾‾‾]

194B

Patient History

☐ Chronic Lung Disease
☐ Dyslipidemia
☐ On Home O2
☐ Hypertension
☐ Perm Pacemaker
☐ Previous Valve Surgery
☐ PAD – AAA
☐ PAD – Lower Ext
☐ PAD – Renal
☐ PAD – Other ☐ Arrythmia
  Arrythmia Type
☐ Current Angina
  Angina Type
☐ Diabetes?
  Diabetes Therapy Creatinine Level ☐☐-☐

☐ Renal Failure Current

Date of Admission: ☐☐/☐☐/☐☐☐☐   Same Day Elective Admit? ☐ Y ☐ N

Date of Surgery: ☐☐/☐☐/☐☐☐☐

Date of Discharge: ☐☐/☐☐/☐☐☐☐

Initial ICU Visit: ☐ Y ☐ N         Re-admission to ICU: ☐ Y ☐ N

If Yes, Initial ICU Hrs: ☐☐☐☐      If Yes, Additional Hrs: ☐☐☐☐

Page

② ③ ④ ⑤ ⑥ ⑦    

*FIG. 7*

| SMCSR | ACC LHC/PCI Data Form |
|---|---|

MRN: ☐☐☐ - ☐☐ - ☐☐ - S R

First Name: ☐☐☐☐☐☐☐☐☐☐☐☐☐☐☐☐☐☐☐☐☐☐☐

Last Name: ☐☐☐☐☐☐☐☐☐☐☐☐☐☐☐☐☐☐☐☐☐☐☐

Admission Date: 📅 ☐☐/☐☐/☐☐☐☐

Admission
Admission Status:

Cath Lab Visit
Procedure Date/Time: 📅 ☐☐/☐☐/☐☐☐☐ ☐☐:☐☐

| | | |
|---|---|---|
| Right Heart Cath: | ☐ Yes ☐ No | |
| Left Heart Cath: | ☐ Yes ☐ No | |
| PCI Procedure: | ☐ Yes ☐ No | |
| IABP: | ☐ Yes ☐ No | IABP Timing: |
| LV Function Assessed: | ☐ Yes ☐ No | LV Wall Motion: |

Diagnostic Cath Status
PCI Status

| | |
|---|---|
| Cardiogenic Shock: | ☐ Yes ☐ No |
| Non-Invasive Test: | ☐ Yes ☐ No |
| Outcome: | ☐ Positive ☐ Negative ☐ Equivocal |
| Diabetes: | ☐ Yes ☐ No |
| Diabetes Control: | |

History and Risk Factors  To set all to No, click HERE ☐

| | | | |
|---|---|---|---|
| Previous MI (>7 days): | ☐ Yes ☐ No | Peripheral Vascular Disease: | ☐ Yes ☐ No |
| CHF – Previous History: | ☐ Yes ☐ No | Chronic Lung Disease: | ☐ Yes ☐ No |
| Previous Valve Surgery: | ☐ Yes ☐ No | Hypertension: | ☐ Yes ☐ No |
| Previous Cardiac Transplant: | ☐ Yes ☐ No | Dyslipidemia: | ☐ Yes ☐ No |
| Cerebrovascular Disease: | ☐ Yes ☐ No | Family HX CAD – Age < 55: | ☐ Yes ☐ No |

Renal Failure:  ☐ Yes ☐ No
  Dialysis: ☐ Yes ☐ No
Previous PCI  ☐ Yes ☐ No  📅 ☐☐/☐☐/☐☐☐☐
Previous CAB  ☐ Yes ☐ No  📅 ☐☐/☐☐/☐☐☐☐

Page 1      ②③④⑤ Next Page

*FIG. 8*

JCAHO Core Measure Questions: Acute MI

| Admission Source | | | |
|---|---|---|---|
| Admission Type | | | |
| Transferred from another ED ☐ Yes ☐ No | | | |
| Arrival Date 📅 ☐☐/☐☐/☐☐☐☐ | | Arrival Time (military) ☐☐☐☐ | |
| Time EKG Performed ☐☐:☐☐ | | Initial ECG Interpretation | ☐ Yes ☐ No |
| Aspirin 24 before or after arrival | ☐ Yes ☐ No | Contrained to aspirin on arrival | ☐ Yes ☐ No |
| Beta blocker within 24 hours after arrival | ☐ Yes ☐ No | Contrained to beta blocker on arrival | ☐ Yes ☐ No |
| Fibrinolytic administration: | ☐ Yes ☐ No | Reason for delay in fibrinolytic tx | ☐ Yes ☐ No |
| Fibrinolytic admin date 📅 ☐☐/☐☐/☐☐☐☐ | | Fibrinolytic admin time ☐☐☐☐ | |
| First PCI Date 📅 ☐☐/☐☐/☐☐☐☐ | | First PCI Time ☐☐☐☐ | |
| Non-primary PCI | ☐ Yes ☐ No | Reason for delay in PCI | ☐ Yes ☐ No |
| Was PCI performed Successfully? | ☐ Yes ☐ No | | |
| Aspirin prescribed at discharge | ☐ Yes ☐ No | Contrained to aspirin at discharge | ☐ Yes ☐ No |
| ACEI prescribed at discharge | ☐ Yes ☐ No | Contrained to ACEI at discharge | ☐ Yes ☐ No |
| ARB prescribed at discharge | ☐ Yes ☐ No | Contrained to ARB at discharge | ☐ Yes ☐ No |
| Beta blocker prescribed at discharge | ☐ Yes ☐ No | Contrained to beta blocker at discharge | ☐ Yes ☐ No |
| Lipid-Lowering Agent Rx at D/C | ☐ Yes ☐ No | LVSD | ☐ Yes ☐ No |
| Adult smoking history | ☐ Yes ☐ No | Adult smoking counseling | ☐ Yes ☐ No |
| Discharge Status: | | | |

Demographics Concurrent Review

Core Measures

JCAHO Core Measure Questions: Heart Failure

| Admission Source | |
|---|---|
| Admission Type | |

| | | | |
|---|---|---|---|
| Adult smoking history | ☐Yes ☐No | Adult smoking counseling | ☐Yes ☐No |
| LVSF assessment | ☐Yes ☐No | LVSD | ☐Yes ☐No |
| ACEI prescribed at discharge | ☐Yes ☐No | ARB prescribed at discharge | ☐Yes ☐No |
| Contraind to ACEI at discharge | ☐Yes ☐No | Contraind to ARB at discharge | ☐Yes ☐No |

Discharge Status:

| | | | |
|---|---|---|---|
| Activity addressed at discharge | ☐Yes ☐No | Diet counseling at discharge | ☐Yes ☐No |
| Follow-up MD listed at discharge | ☐Yes ☐No | Medications reconciled at discharge | ☐Yes ☐No |
| Symptoms worsening addressed at discharge | ☐Yes ☐No | Weight monitoring addressed at discharge | ☐Yes ☐No |

STROKE PATIENT DATA                                     198B

Consultations ─────────────────────────────────────

Patient Assessed or Received Rehab Service ☐ Yes ☐ No ☐ Not Documented

If "Yes," what type?
                                        | Additional Consultation |

Acute Interventions This Hospital ───────────────── t-PA Given?    ☐ Yes ☐ No If "Yes," Date/Time 📅 ☐☐/☐☐/☐☐☐☐ ☐☐:☐☐

Dysphasia screen
Performed prior ☐ Yes ☐ No If "Yes," Date/Time 📅 ☐☐/☐☐/☐☐☐☐ ☐☐:☐☐
to oral intake?

Reason for not screening:

| Other Diagnostic/Interventional Procedures |   | Additional Intervention |
|---|---|---|
| | | Complications |

Contraindications/Reason IV t-PA Not given at this hospital ─────

| | | | |
|---|---|---|---|
| Delay in Patient Arrival | ☐ Yes ☐ No | Abnormal PPT or OT | ☐ Yes ☐ No |
| Delay CT Ordered to CT Done | ☐ Yes ☐ No | Glucose < 50mg/dl or >400mg/dl | ☐ Yes ☐ No |
| Delay CT Done to CT Read | ☐ Yes ☐ No | | |
| Other Time Delay | ☐ Yes ☐ No | Age | ☐ Yes ☐ No |
| Uncontrolled Hypertension | ☐ Yes ☐ No | Investigational Protocol Instead of IV t-PA | ☐ Yes ☐ No |
| Rapid Improvement | ☐ Yes ☐ No | | |
| CT Findings | ☐ Yes ☐ No | IV t-PA Offered but Patient/Family Refused | ☐ Yes ☐ No |
| Recent Surgery/Trauma (<15 days) Recent IC Surgery, Head Trauma | ☐ Yes ☐ No | IC Hemorrhage, Aneurysm, Brain Tumor or Vascular Malformation | ☐ Yes ☐ No |
| or Stroke (<3 months) | ☐ Yes ☐ No | Active Internal Bleeding (<22 days) | ☐ Yes ☐ No |
| Seizure at Onset | ☐ Yes ☐ No | Life Expectancy <1 Year or Sever Co-Morbidity | ☐ Yes ☐ No |
| No IV Access | ☐ Yes ☐ No | | |
| Consent Not Obtainable | ☐ Yes ☐ No | IV t-PA Given at Other Hospital Prior to Transfer | ☐ Yes ☐ No |
| Platelet Count (<100,00) | ☐ Yes ☐ No | | |
| | | Other | ☐ Yes ☐ No |
| Stroke Severity | | Not Documented | ☐ Yes ☐ No |

DVT Prophylaxis ─────────────────────────────────

Patient ambulatory at the end of hospital day 2? ☐ Yes ☐ No
DVT prophylaxis initiated by end of hospital day 2? ☐ Yes ☐ No ☐ NA

| Next Page |

*FIG. 11*          1  3

STS Data Form v2.52

Medical Record#: ☐☐-☐☐-☐☐-☐☐    Social Sec #: ☐☐☐-☐☐-☐☐☐☐

Patient's Last Name: ☐☐☐☐☐☐☐☐☐☐☐☐☐☐☐

Patient's First Name: ☐☐☐☐☐☐☐☐☐☐☐☐☐☐☐☐☐☐☐  M.I.: ☐

Patient Address: ☐☐☐☐☐☐☐☐☐☐☐☐☐☐☐☐☐☐☐

City: ☐☐☐☐☐☐☐☐☐☐☐☐☐☐☐☐☐☐

State: ☐☐    Patient Phone: (☐☐☐) ☐☐☐-☐☐☐☐

Date of Birth: (MM/DD/YYYY) ☐☐/☐☐/☐☐☐☐

Gender:  ☐ Male  ☐ Female    Race: [_____]

---

DRG ☐☐☐☐

Payor: [_____]

Date of Admission: 📅 ☐☐/☐☐/☐☐☐☐

Date of Surgery: 📅 ☐☐/☐☐/☐☐☐☐

Date of Discharge: 📅 ☐☐/☐☐/☐☐☐☐

Initial ICU Visit:  ☐ Y  ☐ N
  If Yes, Initial ICU Hrs: ☐☐☐☐

Readmission to ICU:  ☐ Y  ☐ N
  If Yes, Additional Hrs: ☐☐☐☐

Date of ICU Discharge: 📅 ☐☐/☐☐/☐☐☐☐

Time of ICU Discharge: ☐☐:☐☐

Tabs: Demographics Hospitalization | Risk Factors | Preoperative Status | Preop Meds Hemodynamics & Cath | Operative | Postoperative Complications | Discharge Readmission

| SMCSR | ACC LHC Data Form |
|---|---|

MRM: [4][4]4 - [8][8] - [7][7] - SR

First Name: [L][I][S][A]

Last Name: [T][E][S][T][P][C][I]

Admission Date: 📅 [1][0] / [1][1] / [2][0][0][6]

Admission
  Admission Status: [Other]

Cath Lab Visit
Procedure Date/Time: 📅 [1][0] / [1][1] / [2][0][0][6]  [0][8]:[0][0]
Right Heart Cath         ◉ Yes  ☐ No
Left Heart Cath          ◉ Yes  ☐ No
IABP                     ☐ Yes  ◉ No   IABP Timing [          ]
LV Function Assessed     ◉ Yes  ☐ No   LV Wall Motion [Normal]
Percutanious Entry Location [No Arterial Catheter]

History and Risk Factors    To set all to No, click HERE ☐

| | | | | |
|---|---|---|---|---|
| Previous MI (>7 days): | ☐ Yes ◉ No | Peripheral Vascular Disease: | ☐ Yes ◉ No |
| CHF-Previous History: | ☐ Yes ◉ No | Chronic Lung Disease: | ☐ Yes ◉ No |
| Previous Valve Surgery: | ☐ Yes ◉ No | Hypertension: | ☐ Yes ◉ No |
| Previous Cardiac Transplant: | ☐ Yes ◉ No | Dyslipidemia | ☐ Yes ◉ No |
| Cardiovascular Disease: | ☐ Yes ◉ No | Family HX CAD-Age < 55: | ☐ Yes ◉ No |

Renal Failure:              ☐ Yes ◉ No
          Dialysis  ☐ Yes ☐ No

Previous PCI:     ☐ Yes ◉ No    📅 [  ] / [  ] / [     ]
Previous CAB:     ☐ Yes ◉ No    📅 [  ] / [  ] / [     ]

Cardiac Status
  CHF (Current Status): ☐ Yes ☐ No    NYHA: ☐ I  ☐ II  ☐ III  ☐ IV Admission Sx Presentation
  If Non-STEMI or
    STEMI, Time Period Page 1

*FIG. 15*

Patient Last Name: TESTPCI

Coronary Anatomy

|  | Native Arteries | | Graft | |
|---|---|---|---|---|
|  | Assessed | % Stenosis | Assessed | % Stenosis |
| Left Main: | ☐ Yes ☐ No | ☐☐☐ | | |
| Prox LAD: | ☐ Yes ☐ No | ☐☐☐ | ☐ Yes ☐ No | ☐☐☐ |
| Mid/Distal LAD | ☐ Yes ☐ No | ☐☐☐ | ☐ Yes ☐ No | ☐☐☐ |
| Circumflex: | ☐ Yes ☐ No | ☐☐☐ | ☐ Yes ☐ No | ☐☐☐ |
| RCA/PDA | ☐ Yes ☐ No | ☐☐☐ | ☐ Yes ☐ No | ☐☐☐ |
| Ramus: | ☐ Yes ☐ No | ☐☐☐ | ☐ Yes ☐ No | ☐☐☐ |

230

Diagnostic Cath Procedure

Diagnostic Cath Status [           ]

Indications:  Valvular Heart Disease ■ Yes ☐ No    Arrhythmia    ■ Yes ☐ No
        R/O CAD:         ■ Yes ☐ No    Positive Stress Test ■ Yes ☐ No
        Other Diagnostic   ■ Yes ☐ No
        Cath Indications:              Other Misc [Preop Evaluation]
        Other Cardiac [Congenital Heart Disease]  Indications:
        Indications:
        Transplant:  [Donor for Cardiac Transplant]

Adverse Outcomes

General Complications            Vascular/Bleeding Complications
No Complications ☐               No Complications ☐
Periprocedural MI:    ■ Yes ☐ No    Bleeding at Purcutainious Entry Site: ■ Yes ☐ No
Cardiogenic Shock:    ■ Yes ☐ No    Retroperitoneal Bleeding:           ■ Yes ☐ No
CHF:                  ■ Yes ☐ No    Gastrointestinal Bleeding:          ■ Yes ☐ No
CVA/Stroke:           ■ Yes ☐ No    Genital/Urinary Bleeding:           ■ Yes ☐ No
Tamponede:            ■ Yes ☐ No    Bleeding Other/Unknown Case         ■ Yes ☐ No
Thrombocytopenia:     ■ Yes ☐ No    Access Site Occlusion:              ■ Yes ☐ No
Contrast Reaction:    ■ Yes ☐ No    Peripheral Embolization:            ■ Yes ☐ No
Renal Failure:        ■ Yes ☐ No    Dissection:                         ■ Yes ☐ No
Emergency PCI:        ■ Yes ☐ No    Pseudoaneuryism:                    ■ Yes ☐ No
                                        If Yes, Treatment:  [Pressure]
                                    AV Fistula:                         ■ Yes ☐ No

Cardiac Status

CABG this Admission: [Transferred for CABG]   Date: 🗓 [1][0]/[2][3]/[2][0][0][6]
Discharge Status:    [Alive]            Discharge Date: 🗓 [1][0]/[2][4]/[2][0][0][6]
If Dead,
   Date of Death 🗓 [ ][ ]/[ ][ ]/[ ][ ][ ][ ]   Primary Cause [                ]
                                              Of Death:
   Death in Lab:   ☐ Yes ☐ No

*FIG. 16*   ①   [Prev Page]

Last Name [_____] [__]
MR # [_____]

FIG. 17

Last Name [JONES_____]   Account # [4623200000]
MR # [1654320__]

FIG. 18

Admission Date [🗓 12/25/2007]   Discharge Date [🗓 05/29/2007] — 234

FIG. 19

| Ejection Fraction Done: ●Y ☐N   If Yes, EF %: [88]   If Yes, Method: [LV Gram ▾] | — 236

FIG. 20

| Ejection Fraction Done: ●Y ☐N   If Yes, EF %: [80]   If Yes, Method: [LV Gram ▾] | — 236

FIG. 21

| | | |
|---|---|---|
| Concurrent Review | ☐ Yes | ☐ No |
| CHF Care Plan | ☐ Yes | ☐ No |
| CHF Home Instruction Sheet | ☐ Yes | ☐ No  ~240 |
| CHF Measure D/C Screen | ☐ Yes | ☐ No |
| Core Measure Doc Initiated | ☐ Yes | ☐ No |

Figure 22

| | | |
|---|---|---|
| Concurrent Review | ☒ Yes  ~242 | ☐ No |
| CHF Care Plan | ☐ Yes | ☐ No |
| CHF Home Instruction Sheet | ☐ Yes | ☐ No |
| CHF Measure D/C Screen | ☐ Yes | ☐ No |
| Core Measure Doc Initiated | ☐ Yes | ☐ No |

Figure 23

| | | |
|---|---|---|
| Concurrent Review | ☐ Yes | ☒ No  ~244 |
| CHF Care Plan | ☐ Yes | ☐ No |
| CHF Home Instruction Sheet | ☐ Yes | ☐ No |
| CHF Measure D/C Screen | ☐ Yes | ☐ No |
| Core Measure Doc Initiated | ☐ Yes | ☐ No |

Figure 24

| | |
|---|---|
| Congestive Heart Failure: | ☐ Y  ☐ N |
| ⟨NYHA Classification:⟩ | ☐ I  ☐ II  ☐ III  ☐ IV |
| Angina: | ☐ Y  ☐ N    If Yes, Type: ☐ Stable  ☐ Unstable |
| CCS Classification: | ☐ Class 0  ☐ Class I  ☐ Class II  ☐ Class III  ☐ Class IV |

*FIG. 25*

| | |
|---|---|
| ~~NYHA Classification:~~ | ☐ I  ☐ II  ☐ III  ☐ IV |
| Angina: | ☐ Y  ☐ N    If Yes, Type: ☐ Stable  ☐ Unstable |

*FIG. 26*

STS Field Definitions

Field: Classifications – NYHA

Seq No: 870 -- Shrt Name: ClassNYH
Apollo Field Name: STS_History.NYHA

Indicate the New York Heart Association Class. NYHA classification represents the overall functional status of the patient in relationship to both congestive heart failure and angina. Code the highest class leading to episode of hospitalization and/or procedure.
Class I = Patients with cardiac disease but without resulting limitation of physical activity. Ordinary physical activity does not cause undue fatigue, palpitation, dyspnea, or anginal pain.
Class II = Patients with cardiac disease resulting in slight limitation of physical activity. They are comfortable at rest. Ordinary physical activity results in fatigue, palpitations, dyspnea, or anginal pain.
Class III = Patients with cardiac disease resulting in marked limitation of physical activity. They are comfortable at rest. Less than ordinary physical activity results in fatigue, palpitations, dyspnea, or anginal pain.
Class IV=Patients with cardiac disease resulting in inability to carry on any physical activity without discomfort. Symptoms of cardiac insufficiency of the anginal syndrome may be present even at rest. If any physical activity is undertaken, discomfort is increased.

FIG. 27

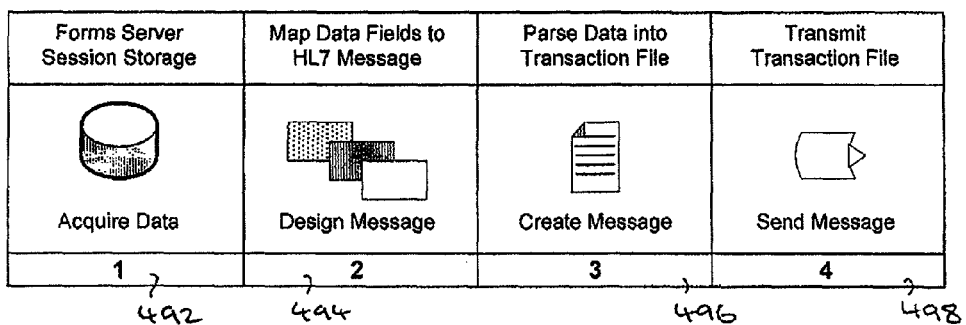

| Forms Server Session Storage | Map Data Fields to HL7 Message | Parse Data into Transaction File | Transmit Transaction File |
|---|---|---|---|
| Acquire Data | Design Message | Create Message | Send Message |
| 1 | 2 | 3 | 4 |
| 492 | 494 | 496 | 498 |

Figure 34

```
Sample HL7 file layout (first 18 lines of 30 line file):
MSH|^~\&|APOLLO|SUTTER|MIDAS|CPMC|20070405093022||ORU^R01|TF0000970|P|2.3|||||||
PID|||000995777||TESTCASE^LEONIDAS^C|||||||||A1224399|||||||||||
OBR|1|||AMI|||20070405093022|20070405093022|||||||||||||||||||||||||||||||
OBX|1|ST|ACEI_Disch||Yes|||||||20070405093022|||
OBX|2|ST|Adult_Smoking_Counseling||Yes|||||||||20070405093022|||
OBX|3|ST|Adult_Smoking_History||Yes|||||||20070405093022|||
OBX|4|ST|ARB_Disch||Yes|||||||20070405093022|||
OBX|5|DT|Arrival_Date||20070405||||||||20070405093022|||
OBX|6|TM|Arrival_Time||0920|||||||20070405093022|||
OBX|7|ST|Aspirin_Arr||Yes|||||||20070405093022|||
OBX|8|ST|Aspirin_Disch||Yes|||||||20070405093022|||
OBX|9|ST|BetaBlocker_Arr||Yes|||||||20070405093022|||
OBX|10|ST|BetaBlocker_Disch||Yes|||||||20070405093022|||
OBX|11|ST|Comfort_Measures||No|||||||20070405093022|||
OBX|12|ST|Contraind_ACEI_ARB||No|||||||20070405093022|||
OBX|13|ST|Contraind_Aspirin_Arr||No|||||||20070405093022|||
OBX|14|ST|Contraind_Aspirin_Disch||No|||||||20070405093022|||
OBX|15|ST|Contraind_BetaBlocker_Arr||No|||||||20070405093022|||
OBX|16|ST|Contraind_BetaBlocker_Disch||No|||||||20070405093022|||
```

Figure 35  510

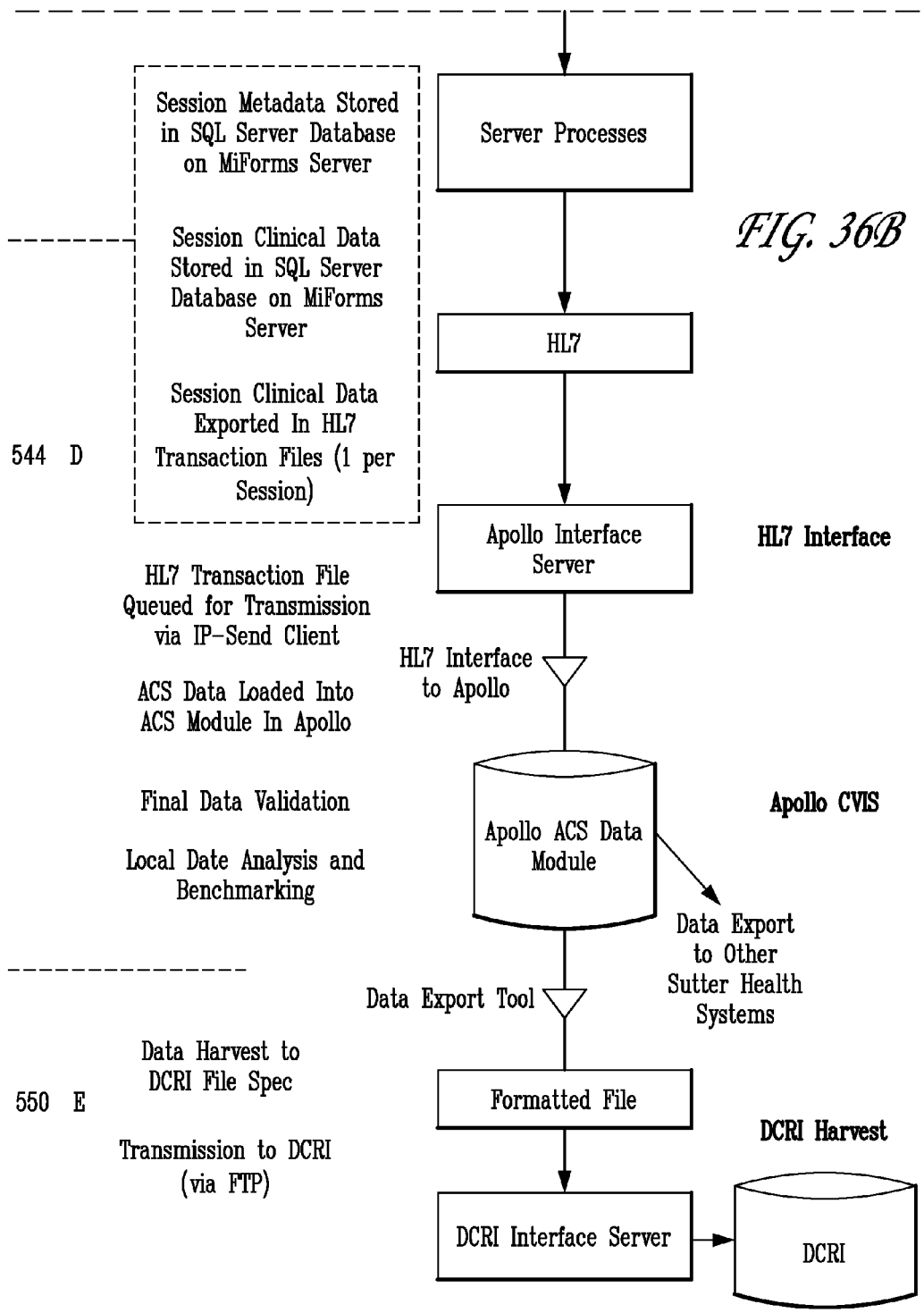

National Cardiovascular Data Registry
current and proposed registries

| | | | | | | Ped. Registry | |
| --- | --- | --- | --- | --- | --- | --- | --- |
| | | | | Achieve | | EP Registry | |
| | | | | ICD Long | | PracMgt Registry | |
| | | | | *Imaging Registry* | | PAD Registry | |
| | | | | *Composite Registry* | IC3 CAD | HF Registry | |
| | | | | ACTION Registry | | | |
| | | | CARE Registry | | | | |
| CathPCI Registry | | ICD Registry | | | | | |
| 1998... | 2004 | 2005 | 2006 | 2007 | 2008 | 2009... | |

SYSTEM AND METHOD FOR DATA COLLECTION AND MANAGEMENT

CROSS REFERENCE TO RELATED APPLICATIONS

This application is a continuation and claims the benefit of International Application number PCT/US2008/008092, filed Jun. 27, 2008 and entitled "System and Method for Data Collection and Management," which claims the priority benefit of Provisional Patent Application No. 60/948,635, filed Jul. 9, 2007 and entitled "System and Method for Data Collection and Management," each of which is incorporated by reference herein.

BACKGROUND

1. Field of the Invention

Various aspects are generally related to data management, and specifically to systems and methods for collecting, validating, managing, and sharing data between portable devices, central servers, and third-party entities. In accordance with some embodiments, the system can be used in a healthcare, inpatient, or an ambulatory care setting, or at another point of care or location.

2. Description of Related Art

Within the healthcare industry, the need for healthcare institutions, such as hospitals, clinics, and other health-related facilities to collect high-quality patient and other data is of paramount importance. However, the need to accurately collect such data, combined with the limited resources of many institutions, has caused considerable strain in the industry as governmental agencies, HMOs, healthcare payors, and accrediting bodies nationwide place increasing demands on those institutions to ensure the quality of their data.

Today, inefficient paper-based data collection processes are still ubiquitous in hospitals. It is common for the same piece of clinical information or patient data to be collected multiple times by multiple people, and in multiple different hospital departments, during the course of a patient's hospitalization. To ensure quality and adequate treatment of each patient, it is imperative that the right information be collected by the right person at the right time, and as close as possible to the point of care. This reduces redundancy, and improves the overall efficiency of data collection and retrieval. The current paper-based processes also pose potential legal liabilities for healthcare institutions, because of the risk of duplicate data that is inconsistent or that conflicts with one another. Secondary effects of paper-based collection must also be considered. For example, there may be a potential compromise of patient care due to the diversion of clinician resources that are expended to collect certain mandated data, whether that data is really beneficial to the patient or not. A healthcare institution may also suffer marketing impacts, and the potential loss of contracting opportunities, and opportunities to market clinical services, unless they can provide high quality patient data and treatment data to support their claimed standard of care.

However, to date no current system allows for quick and accurate electronic collection of data concurrent with the process of healthcare delivery with instant data validation, while providing the flexibility to then provide that data automatically to any of a number of different departments, organizations, or clinical entities. This is the area the present invention is intended to address.

SUMMARY

Described herein is a system and method for collecting, validating, managing, and sharing data, for example healthcare and patient data, using a portable device. As disclosed herein the system allows for concurrent collection of data using mobile handheld devices at the point of data collection. In the context of healthcare this can be, for example at a hospital patient's bedside, or in a physician's office, or at another point of care. Data can be instantly validated via embedded clinical rules logic, using forms that are customized to the particular needs of one or more healthcare applications. The system is also flexible in that it allows data to be provided to any of a number of different departments, organizations, or clinical entities. The forms-based system and process (referred to in some embodiments as DirectForms™ allows clinical staff to efficiently collect and instantly validate data on portable tablet PCs, and subsequently send the data to local servers or clinical systems, national data registries, or other entities. The system is particularly well suited for use in healthcare settings at or near the point of care, which reduces data collection errors and increases overall efficiency. In accordance with an embodiment, the system combines a computing device including but not limited to a computer, a portable computer, a tablet PC, a Personal Digital Assistant, a mobile phone, or other electronic device, penbased data entry, immediate validation of data, network connectivity, and shared effort among members of a user workgroup with transmission to servers, clinical databases, or other entities via industry-standard (for example HL7 or "Health Level Seven" compliant) or customized interfaces. In accordance with an embodiment, the system uses a combination of tablet PC technology and a forms-based software product to provide a powerful mobile handwriting-based digital data capture system, which runs on tablet PCs, Anoto-enabled pens, Windows Mobile Pocket PCs or other mobile devices. Data collected on the tablet PC can be immediately validated using system and custom rules, including clinical business rules and field-specific logic. A server-based software provides intelligent routing of forms and HL7 compliant data transaction exports. Interfaces to clinical database systems and national registries provide the ability to merge the data into appropriate patient records. Use of the forms-based approach translates to considerable cost savings for the hospital or healthcare institution in collecting data, together with the ability to provide and guarantee the accuracy of that data for purposes of contracting and marketing. In accordance with other embodiments, the system can be used in an ambulatory care setting, or in a physician or other external office. The various benefits and advantages of these systems and techniques include improved clinical assessment, effective patient management, cost savings with regard to data collection, and the ability to provide a more efficient billing process.

BRIEF DESCRIPTION OF THE FIGURES

FIG. 4 illustrates an example of a form in accordance with an embodiment.

FIG. 5 illustrates another example of a form in accordance with an embodiment.

FIG. 6 shown as FIGS. 6A and 6B illustrate examples of a form in accordance with embodiments.

FIG. 7 illustrates another example of a form in accordance with an embodiment.

FIG. 8 illustrates another example of a form in accordance with an embodiment.

FIG. 9 illustrates another example of a form in accordance with an embodiment.

FIG. 10 illustrates another example of a form in accordance with an embodiment.

FIG. 11 illustrates another example of a form in accordance with an embodiment.

FIG. 12 illustrates another example of a form in accordance with an embodiment.

FIGS. 15-16 illustrate an example of a form as displayed on a tablet PC in accordance with an embodiment.

FIGS. 17-27 illustrate examples of form dialogs as displayed on a tablet PC in accordance with an embodiment.

FIG. 34 illustrates a message based export in accordance with an embodiment.

FIG. 35 illustrates a HL7 message export in accordance with an embodiment.

FIG. 37 illustrates an acute care data flow model in accordance with an embodiment.

FIG. 38 illustrates an ambulatory data flow model in accordance with an embodiment.

FIG. 40 illustrates a remote server data flow model in accordance with an embodiment.

FIG. 44 illustrates a variety of Cardiac Database registries in accordance with an embodiment.

DETAILED DESCRIPTION

Figure 1:
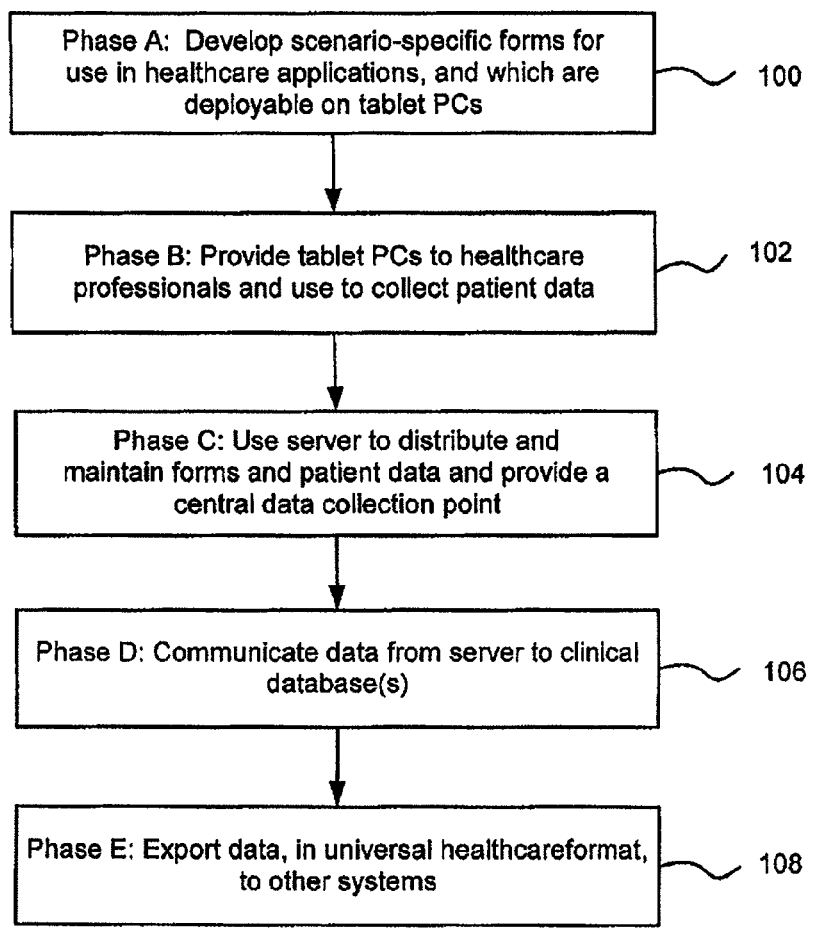
FIG. 1 illustrates the phases of providing healthcare data collection and management using a portable device in accordance with an embodiment.

Within the healthcare industry, the need for healthcare institutions, such as hospitals, clinics, physician offices and other health-related facilities to collect high-quality patient and other data is of paramount importance. However, the need to accurately collect such data, combined with the limited resources of many institutions, has caused considerable strain in the industry as governmental agencies, HMOs, healthcare payors, and accrediting bodies nationwide place increasing demands on those institutions to ensure the quality of their data. Today, inefficient paper-based data collection processes are still ubiquitous in hospitals. It is common for the same piece of clinical information or patient data to be collected multiple times by multiple people, and in multiple different hospital departments, during the course of a patient's hospitalization.

Described herein is a system and method for collecting, validating, managing, and sharing data, for example healthcare and patient data, using a portable device. As disclosed herein the system allows for concurrent collection of data using mobile handheld devices at the point of care, for example at a hospital patient's bedside, or in a physician's office, or at another point of care. Data can be instantly validated using forms that are customized to the particular needs of one or more healthcare applications. The system is also flexible in that it allows data to be provided to any of a number of different departments, organizations, or clinical entities. The forms-based system and process (referred to in some embodiments as DirectForms™ allows clinical staff to efficiently collect and instantly validate data on portable tablet PCs, and subsequently send the data to local servers or clinical systems, national data registries, or other entities. Forms can be designed to collect a set of data that matches the requirements of the receiving entity. The system is particularly well suited for use in healthcare settings at or near the point of care, which reduces data collection errors and increases overall efficiency. In accordance with an embodiment, the system combines a portable computer, pen-based data entry, immediate validation of data, network connectivity, and shared effort among members of a user work group with transmission to servers, clinical databases or other entities via industry-standard (for example HL7 or "Health Level Seven" compliant) or customized interfaces. In accordance with an embodiment, the system uses a combination of tablet PC technology and a forms-based software product to provide a powerful mobile handwriting-based digital data capture system, which runs on tablet PCs, Anoto-enabled pens, Windows Mobile Pocket PCs or other mobile devices. Data collected on the tablet PC can be immediately validated using system and custom rules, including clinical business rules and field-specific logic. A server-based software provides intelligent routing of forms and HL7 compliant data transaction exports. Interfaces to clinical database systems and national registries provide the ability to merge the data into appropriate patient records. Use of the forms-based approach translates to considerable cost savings for the hospital or healthcare institution in collecting data, together with the ability to provide and guaranteed the accuracy of that data for purposes of contracting and marketing.

In accordance with an embodiment the system comprises a selection of components. Depending on the particular implementation, various components may be used together as part of an overall system or process. Alternatively, a selection of one or more of the components can be employed to handle certain tasks. Additional components can then be added to the system as necessary. In accordance with an embodiment, components may include:

A. Forms Design Component, which blends technical and visual design elements, and allows a company, organization, or healthcare institution such as a hospital, to create forms that meet multiple simultaneous data collection goals for that company, organization or healthcare institution. The form manages the quality of data while it is being entered, and offers simplified navigation throughout the form coupled with speedy data entry.

B. Tablet PC Component, which builds on the inherent portability of tablet PCs, portable computers, stylus-based devices, and the store-and-forward technology represented by the forms; to collect data anywhere in the company; organization, healthcare institution or hospital, tracking multiple customers or patients simultaneously, and collecting data from the many resources involved in active patient care.

C. Forms Server Component, which is configured to manage workflow through work queues and form-specific routing, centralized form revision control, and discrete TCP-IP transmission of the data collected using the forms to receiving clinical systems via HL7-compliant and other transactions and interfaces.

D. Clinical Database Electronic Upload Component, which controls uploads to a Clinical Database of completed and validated data from the tablet PC and forms. The upload component can address multiple clinical repositories simultaneously, as applicable, and merge collected data with existing data records in the context of larger enterprise datasets.

E. Export Component, for export of data to other systems, such as national medical-related, governmental, and other data registries, using export tools specific to each data registry's harvest procedure, or to the needs of the receiving clinical system. The export component can carefully match the receiving system's import file specification, setting a flag in the local clinical database at the server to indicate whether a record has been harvested.

The above components can be used together to provide a system for collecting, validating, managing, and sharing patient and other healthcare data using a portable device. Similarly, each component may be associated with a phase or a sequence of steps, that when performed together provide a method for collecting, validating, managing, and sharing patient and other healthcare data using a portable device.

FIG. 1 illustrates various phases of providing a healthcare data collection and management system using a portable device, in accordance with an embodiment. As shown in FIG. 1, in step 100, Phase A includes developing a scenario-specific or customized form for use in a healthcare application. The form is then deployed onto one or more tablet PCs in a healthcare environment, for example a healthcare institution, hospital, clinic or other healthcare facility. In step 102, in Phase B, the tablet PCs or other portable devices are provided to healthcare professionals for example doctors and nurses, who use the tablet PCs to collect patient data. Examples of data collection may include patient intake data for use in clinical systems, or day-to-day post-surgery patient data collection. In step 104, in Phase C, a central server, or forms server, is used to distribute and maintain forms to the tablet PCs. The server also receives patient data from the tablet PCs, and provides a central data collection point, for subsequent providing of the data to clinical databases and other systems. In accordance with some embodiments the server may include workflow intelligence to ensure the correct people/tablet PCs receive the correct forms and data. In step 106, in Phase D, the data is communicated from the server to one or more clinical databases, either at the same institution, or at another third-party location. Examples of clinical databases include cardiology-related databases, and other clinical databases for use in specialized analysis of the data. In step 108, in Phase E, the data may optionally be exported in a system-specific format for use with other external systems. Examples of other systems include national registries, such as the American College of Cardiology (ACC) National Cardiovascular Data Registry (NCDR) database systems. Optionally, information can be received from the external system and used with the server and the tablet PCs, to further customize the forms that are used in the initial data collection.

Each of the phases are described in further detail below. Also described below are implementations that use a combination of some or all of the components or phases to provide integrated systems for collecting, validating, managing, and sharing patient and other healthcare data in specialized clinical settings.

A. Interactive Form Phase

In accordance with an embodiment, the process begins with a user or a forms developer using a forms design tool to create interactive forms. Each of the forms may in turn incorporate several key elements, for example:

- Arrange the dataset to be collected in a manner that is logical to the operator or data collector that will eventually use the forms, combining elements from several data collection projects, as appropriate, to increase efficiency, and allow one collection effort to cover multiple subjects simultaneously.
- Incorporate checks to ensure the quality of data as it is being entered.
- Data validation rules such as data range checks, validity checks, and enforcing required entry on some fields.
- Data correlation rules to enforce parent-child behavior between related fields, so that an answer in one field prompts or prohibits an answer in a related field.
- Include clinically accurate, context-sensitive help text, which is available to the user with a quick stroke of a stylus.
- Simplified navigation through the form using notebook tabs, navigation arrows, clear form section headings, and an index for locating fields by subject or synonym.
- Included hidden forms or pages that are only presented to the operator if needed, so that users are not needlessly presented with rarely used fields, unless the patient's specific circumstances cause those fields to apply.
- Highlighting of required data fields that are empty, with colored shading and other graphical elements.
- Simplified management of drop-down pick-lists via embedded list files with standardized procedure names, department names or admission locations to ensure standard spellings and to allow central distribution of list updates.
- Selection tools such as pop-up windows to allow the user to readily navigate lists of physician names and make a selection with a click of the stylus.
- Speeded up data entry, including allowing the user to set "default" values with single stroke with zones marked "Click here to set all to No" or similar choices, and pop-up calendars to select dates.

Figure 2:
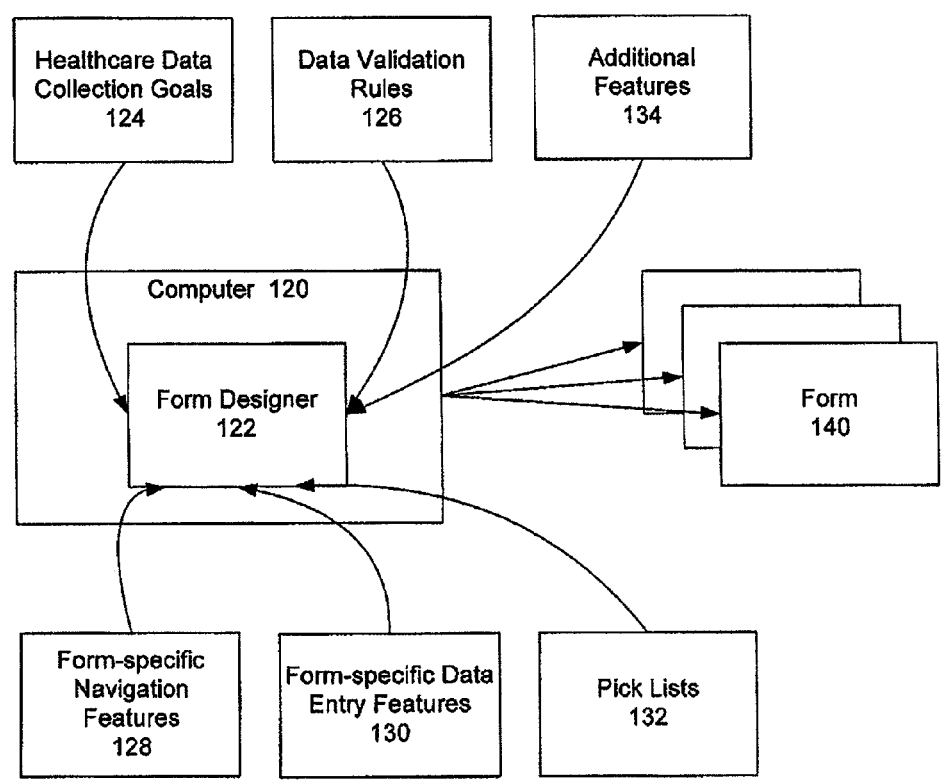
FIG. 2 illustrates the forms phase in accordance with an embodiment.

FIG. 2 illustrates the forms phase in accordance with an embodiment. As shown in FIG. 2, the forms are designed using a form designer 122 which resides on a computer 120 or other systems. Generally, such systems may include a processor, memory, storage media, input and output devices, a power supply, and communications circuitry. The forms designer is used by an individual such as a forms developer, to create application-specific or customized forms which will later be used on the tablet PC in the healthcare environment. As shown in FIG. 2, the form designer uses knowledge of healthcare data collection goals 124 to determine which form items should be included in the form, and which data needs to be collected to suit that particular application. The form designer can also specify data validation rules 126, which are used to ensure the data entered into the form matches the data that is required by the dataset standard or clinical system. In accordance with some embodiments, the form designer may also incorporate form-specific navigation features 128, which provide a more interactive and usable flow to the forms, making the data entry easier for the healthcare professional. Form-specific data entry features 130, may also be incorporated to allow for quicker and easier access to certain form data for the healthcare professional. In accordance with some embodiments the form may include a pick list 132 or additional features 134, for example a list of doctors, hospitals, healthcare providers or patient related information which can be used to quickly complete a form. Once the forms have been designed in the form designer, the finished forms 140 can be output and later used in the tablet PC (or equivalent device) environment.

Figure 3:
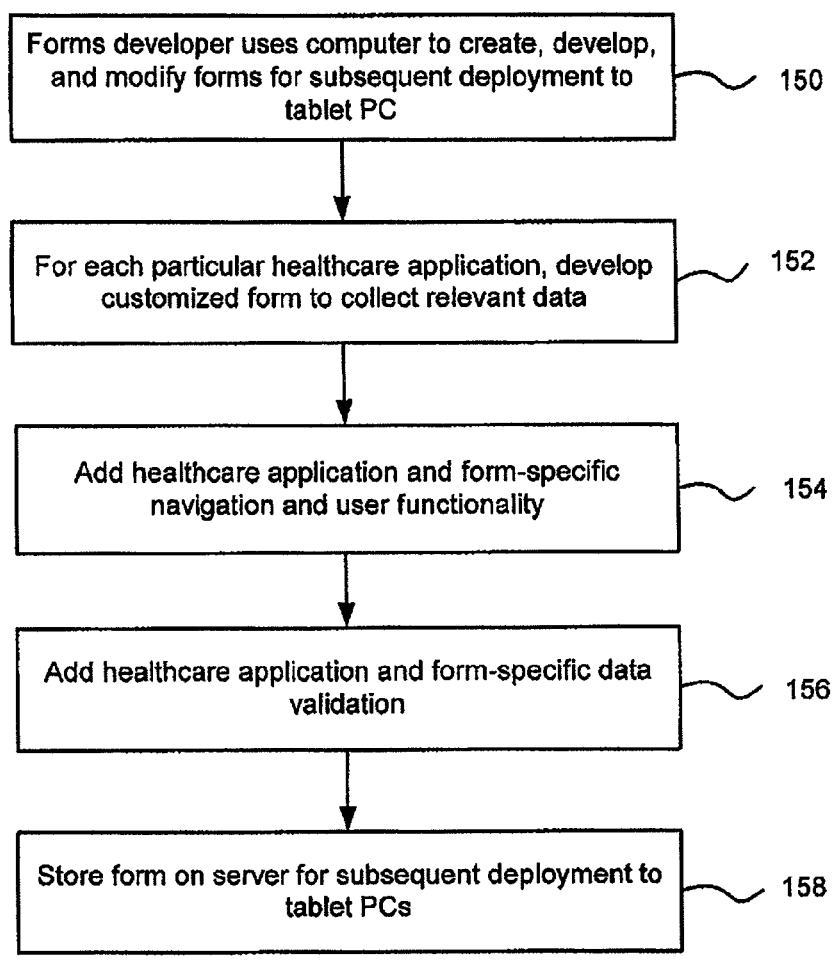
FIG. 3 is a flowchart that illustrates the steps of the forms phase in accordance with an embodiment.

FIG. 3 is a flow chart that illustrates the steps of the forms phase in accordance with an embodiment. As shown in FIG. 3, in step 150 the form developer, such as a software developer or more likely a healthcare professional with information about the type of data that needs to be collected, uses a computer to create, develop and modify forms for subsequent deployment to the tablet PC. In step 152, for each particular healthcare application that the tablet PC will be used for, an application-specific form is a developed and customized to collect the relevant data for that application. In step 154, desired healthcare application and form specific navigation and user functionality can be incorporated. In step 156, healthcare application and form specific data validation can also be included in the form. The navigation, user functionality, and data validation features serve to provide a more intuitive interface to the healthcare professional for adding patient data. Data validation also ensures that the form is complete, and that the answers are consistent with the patient's condition or disease modality. In step 158 the form is stored on a server for subsequent deployment to the tablet PCs.

A wide variety of forms can be provided using the above techniques, some particular examples of which are described below. It will be evident that these examples illustrate the types of forms that can be created, and that other examples and types of forms can be developed within the spirit and scope of the invention.

ACTION National Registry Form

FIG. 4 illustrates an example of a form 170 in accordance with an embodiment. As referred to herein, an ACC-NCDR ACTION Registry form can be provided which includes sections 172, 174, 176, 180 for patient data, presentation features and signs and symptoms of a patient at presentation. The form may also include a number of tabs 178 displayed along the edge of the form which can be selected by the healthcare professional to navigate to additional pages of the form, and to enter data into those pages. As shown in FIG. 4, it will be seen that the interactive form as provided by the computer, largely resembles the paper version of the form that would otherwise be completed by the healthcare professional.

The American College of Cardiology (ACC) has developed the ACTION national clinical database or registry for tracking patients suffering from acute coronary syndrome. The number of data elements that must be collected by ACTION participants is extensive. The current approach is to use paper-based forms, or a Web-based means of data entry: However, it is beneficial for hospitals and other health care institutions to have a data collection method that is significantly more efficient and accurate than the current Web-based system.

In accordance with an embodiment, the DirectForms™ process can be employed to collect, validate and submit ACTION data to the national registry via intelligent interactive forms as prepared during the Forms phase, and subsequently deployed on tablet PC's, PDAs, and portable computers. In this manner the form is designed to capture data in the exact manner required by the ACTION registry. A dedicated server-based or centralized cardiovascular information system, together with an ACC-specific data harvest tool can be used to collect and gather information from multiple tablet PCs and multiple patients. In addition to improvements in efficiency and data quality through this process, institutions such as hospitals and clinics also benefit from an immediate ability to measure patient data and analyze treatment of these patients.

JCAHO Core Measures Form

FIG. 5 illustrates another example of a form 182 in accordance with an embodiment. As shown in FIG. 5, forms can also provide for such requirements as HF Core Measures 184. In the example shown in FIG. 5, the form includes a number of tabbed pages together with information requiring concurrent review questions 186. The Joint Commission on the Accreditation of Healthcare Organizations (JCAHO) has created a series of Core Measures for improvement in the quality of care for acute myocardial infarction and heart failure patients, among others.

The DirectForms™ process can be employed to collect, validate and submit these combined Core Measures data elements with other concurrent review measures so that the clinician can more easily collect all of these data elements at the patient bedside at one time. The interface to the hospital's clinical database automatically sorts the data into Core Measure data and concurrent review data.

In accordance with an embodiment, an interface can be created to provide the patient information to a clinical application approved for reporting Core Measures to the JCAHO. After data collection and validation on the tablet PC, data can be inserted or updated into the JCAHO Core Measure reporting application for the patient after a successful record match on medical record number and encounter number. This provides an electronic path from the tablet PC at the bedside to the Core Measure reporting system.

Multi-Day Surgery Patient Tracking Form

FIGS. 6A and 6B illustrate examples of a form 190 in accordance with embodiments. As shown in FIGS. 6A and 6B, forms can also be provided to track daily surgery flow sheets 192A. For example in FIGS. 6A and 6B, the form is used to track patient data and additional information prior to surgery 194A, on the immediate day of surgery 196A, and on additional days 198A subsequent to the day of surgery. One of the benefits in providing multi-day forms is that the information can be entered on a daily basis into the form, and can be stored for subsequent days so that the information is always in one place even though it spans many days. When the form is complete, (in this instance at the end of the week), then the data stored in the tablet PC or form can be uploaded to the server and used for clinical analysis.

For example, the care of cardiothoracic surgery patients involves monitoring the patients very closely from the day of surgery through all the postoperative days, until discharge from the hospital. Data collected on these patients is analyzed carefully for signs of improvement or change. In accordance with an embodiment, the tablet PC-based tool holds data elements in close visual relationship to one another, on a single screen. This allows clinicians to see changes in lab values or patient weight or other indices, alerting them to critical events occurring during the patient's recovery. Data entry pages can be hidden behind the main page and accessible by form navigation tools, so that the main screen is devoted to presentation of the complete dataset.

ACC Carotid Stent Form

FIG. 7 illustrates another example of a form in accordance with an embodiment. As shown in FIG. 7, forms can be provided to collect and validate information from the patient for use with ACC-NCDR Carotid Stent data collection 194B, wherein the form appears visually similar, or uses sections or fields that match the data collection requirements of the ACC Carotid Stent Form, including sections for patient demographics, patient history, surgical information, and others.

ACC Cath PCI Form

FIG. 8 illustrates another example of a form in accordance with an embodiment. As shown in FIG. 8, forms can be provided to collect and validate information from the patient for use with ACC-NCDR Cath PCI data collection 195, wherein the form appears visually similar, or uses sections or fields that match the data collection requirements of the ACC Cath PCI Form, including sections for patient information, cath lab visits, and history and risk factors, and others.

JCAHO AMI Core Measure Form

FIG. 9 illustrates another example of a form in accordance with an embodiment. As shown in FIG. 9, forms can be provided to collect and validate AMI Core Measures information from the patient 196B, wherein the form appears visually similar, or uses sections or fields that match the data collection requirements of the JCAHO Core Measure Questions Acute MI Form, including sections for admission source and type, EKG, PCI information, and others.

JCAHO HF Core Measure Form

FIG. 10 illustrates another example of a form in accordance with an embodiment. As shown in FIG. 10, forms 197 can be provided to collect and validate Heart Failure Core Measures information from the patient, wherein the form appears visually similar, or Uses sections or fields that match the data collection requirements of the JCAHO HF Core Measure HF Form, including sections for smoking history, diet, medication information, and others.

JCAHO Stroke Form

FIG. 11 illustrates another example of a form in accordance with an embodiment. As shown in FIG. 11, forms 198B can be provided to collect and validate Stroke information from the patient, wherein the form appears visually similar, or uses sections or fields that match the data collection requirements of the JCAHO Stroke Patient Form, including sections for acute interventions, contraindications prophylaxis, and others.

STS Adult CV Surgery Form

FIG. 12 illustrates another example of a form in accordance with an embodiment. As shown in FIG. 12, forms can be provided to collect and validate Adult CV Surgery information from the patient 199, wherein the form appears visually similar, or uses sections or fields that match the data collection requirements of the Society of Thoracic Surgeons (STS) Adult CV Surgery Form, including sections for patient information, hospitalization information, and others.

B. Tablet Data Collection Phase

When the forms are combined with a computer, a portable computing device, tablet PC, PDA, or other portable device, the speed, flexibility and portability of the system allows the user to collect data anywhere, whether in a hospital or in an ambulatory care setting. Features of the tablet data collection phase include:

Store-and-forward technology, which allows the forms to collect and save data on the tablet, until a network contact or other communication with the server is available. The tablet PC's network connection, whether cable or wireless, allows the forms to incorporate database (ODBC) connectivity, to query hospital clinical systems for test results or to perform data lookups. In some embodiments, a feature for downloading updates while the user is entering data reduces redundancy of information. By opening several forms simultaneously on the tablet PC, the operator or user can begin data collection on multiple patients. This means that circulating through the patient care department the user can collect data in "real time" from the many documents, systems and specialists involved in active care for each patient.

Figure 13:
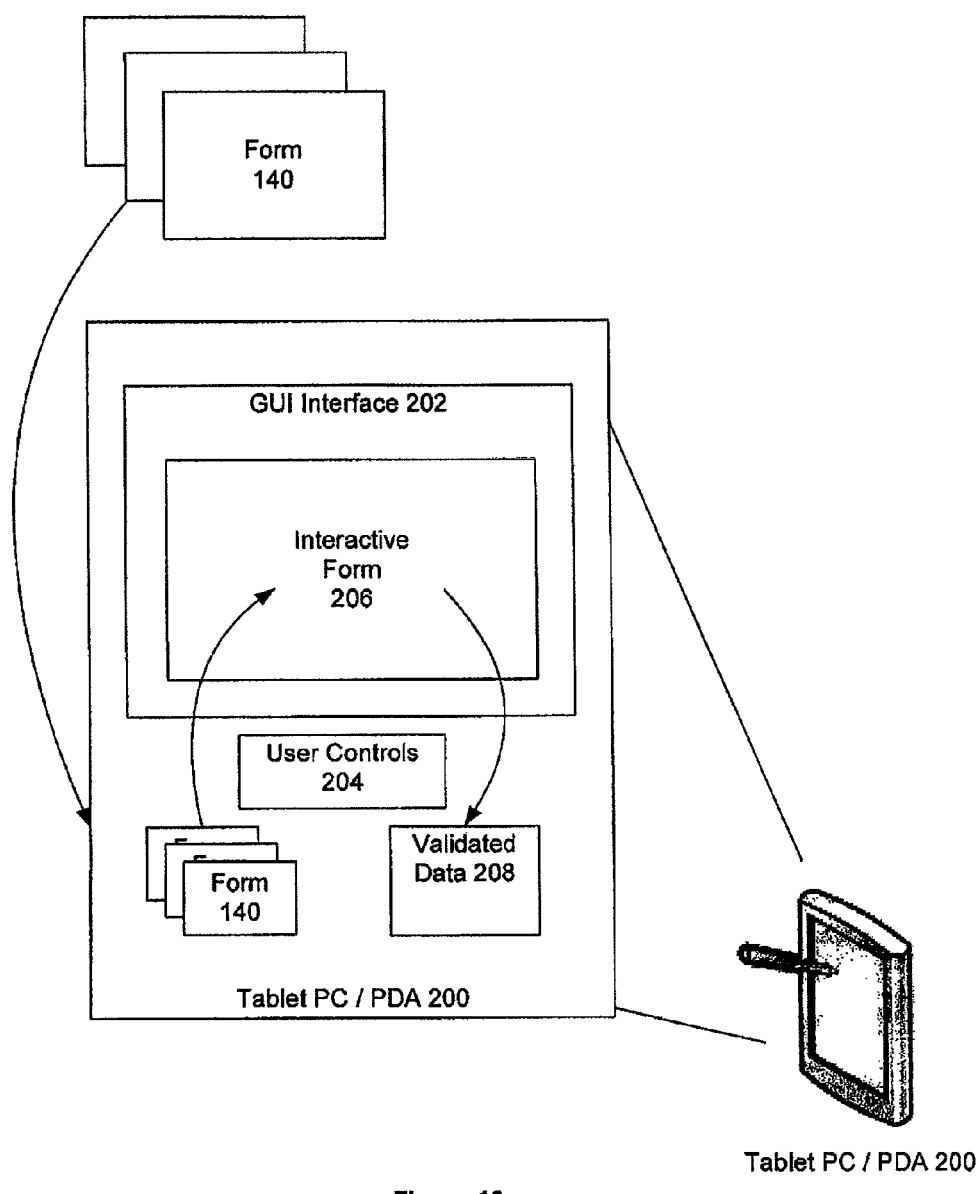
FIG. 13 illustrates the tablet phase in accordance with an embodiment.

FIG. 13 illustrates the tablet phase in accordance with an embodiment. As shown in FIG. 13, the system can be deployed on a tablet PC or PDA 200. Other computer devices may be used, including a desktop computer, laptop computer or other portable computer device. As shown in FIG. 13, the tablet PC includes a user interface 202 together with a number of user controls 204. In accordance with an embodiment the user interface includes a touch screen display or device, and the user controls include one or other pen type devices which are used by the operator to write on the touch screen. In accordance with the embodiment the user interface displays an interactive form on the touch screen display. Forms which have been created during the form deployment phase, are uploaded or in some way distributed or communicated to the tablet PC and stored thereon. The forms stored on the tablet PC are then used to create and display one or more interactive forms 206. Examples of these forms include those shown in FIGS. 4-12 inclusively and described above. As the user enters data on the interactive form, the tablet PC validates and stores the validated data 208 on the tablet PC for subsequent use.

Figure 14:
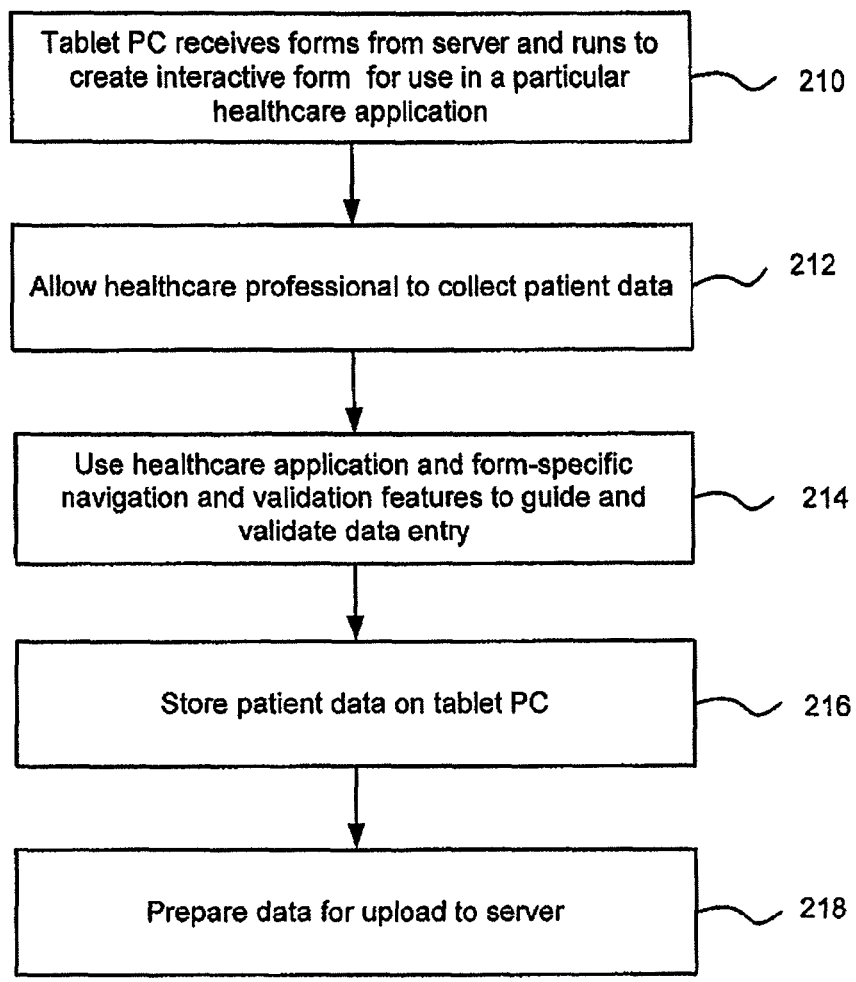
FIG. 14 is a flowchart that illustrates the steps of the tablet phase in accordance with an embodiment.

FIG. 14 is a flow chart that illustrates the steps of the tablet phase in accordance with an embodiment. As shown in FIG. 14, in step 210, the tablet PC receives forms from the server and runs the forms to create an interactive form on the tablet PC, for use in a particular healthcare application. In step 212, the system allows a healthcare professional for example a doctor, nurse, data abstractor, data analyst, clinical researcher or healthcare administrator, to collect patient data or other medical related data. In step 214, the system then uses healthcare application and form-specific navigation and validation features to guide and validate data entry into the forms. One of the advantages over traditional pen and paper method is that the data is validated as it is being entered, so that any error or omission can be quickly noticed and amended. As described below, the form may also include specific features to assist in data entry, including for example hiding certain pages for which data is not needed, or removing options that are not applicable in certain data collection instances. In step 216, the patient data is then stored on the tablet PC, until the tablet PC is able to upload the data to a server or other repository. In step 218 the data is then prepared for upload to the server either using a push/pull technology, or a store and forward means. When the data is stored using a store and forward means, then the data is stored on the tablet PC until access is available to a particular server at which point the data is communicated to that server.

FIGS. 15-16 illustrate an example of form 224 as displayed on tablet PC in accordance with an embodiment. As shown in FIG. 15, page 1 of the form for ACC-NCDR Cath/PCI Registry data form provides fields for entering first name, last name, and other patient related information 226. FIG. 16 shows the second page 230 of the form. One of the benefits of the form shown in FIGS. 15 and 16 are that the form can be completed using a touch pad and stylus, wherein the healthcare professional or person entering data simply writes onto the form as displayed on the screen using a stylus or pen-like device. In this way data can be entered into the form on the tablet PC in a manner identical to how that data would be entered into the paper version of the form. In addition and as an advantage to the paper version, the computer version of the form can be designed to hide features that are not necessary for data entry, and to auto-complete features one or more features have been selected.

FIGS. 17-27 illustrate examples of form dialogs in accordance with embodiments. Instantaneous data validation takes place on the tablet PCs through application of rules to enforce range checks, validity checks and to make data entry required on some fields.

As shown in FIG. 17, the main patient identifiers, last name, medical record number and account number 232, are required and are critical pieces of information, so these form fields are highlighted, for example in a red or other noticeable color.

As shown in FIG. 18, when data is entered, the highlighting disappears. If needed, additional instant data assessment can occur via a database lookup to ensure that, for example, the name and medical record number which the user has entered are known to be valid entries in the hospital's master database.

As shown in FIG. 19, per a form rule, the Date of Admission entered into the form must be earlier than the Date of Discharge 234. In this example the data as entered is invalid, so the form ensures that both fields remain highlighted until one or both entries are corrected.

As shown in FIG. 20, a compound rule is used in this example to say that, if "Ejection Fraction (EF) Done" is marked as "Yes", then a range-check must be enforced 236 on the "EF %" field to ensure that the number entered is between 5 and 85%. Additional rules can be used in the form to enforce additional types of answers, and ranges of answers.

As shown in FIG. 21, by correcting the entry in the "EF %" field, the validation rule is satisfied and the highlighting automatically disappears.

In accordance with an embodiment, the system uses custom data correlation rules to establish and enforce parent-child relationships between related fields so that an answer in one field either prompts or prohibits an answer in a related field. This behavior can be coded into the form, and helps maintain data integrity.

As shown in FIG. 22, in this example, a parent-child type of correspondence exists between specified fields 240 on a form: In this instance if the patient is a candidate for "Concurrent Review" then the four questions which follow are required to be answered.

As shown in FIG. 23, When the user answers "Yes" to the "Concurrent Review" with a mark 242 in the checkbox, then several lines of embedded code are run and several actions take place: in this instance the child fields are unlocked and are prepared to accept an answer; the child fields are highlighted in yellow; and the highlight visually marks the entire series of related fields to guide the user to answer them all in turn. Each of these features helps to ensure that the form is filled out completely by directing the user's attention to additional required data, depending on what is entered into the parent field.

As shown in FIG. 24, in this example if the user answers "No" to the "Concurrent Review" by marking in the appropriate checkbox 244, the embedded Visual Basic code will lock the child fields. This prevents data entry into the child field entirely, since they are to be answered only when the parent field is answered "Yes" and not when it is answered "No."

In accordance with an embodiment, and as shown in the diagrams above, as a normal part of its functionality, the system instantly interprets an ink mark, determining which answer was intended by the user, and marking that answer with a colored (e.g. blue) dot that registers a "Yes" or "No" value in the field. This helps the operator to easily see their answers to the questions. Since data collection at the point of care requires accurate interpretation of the questions, the system also uses a context-sensitive Help tool embedded in the forms on the tablet PC. As shown in FIGS. 25-27, for example, if a clinician wants to use the form to categorize a patient using a widely accepted classification for cardiac disease 250 but finds themselves unfamiliar with the definitions, then by simply making a pen stroke 252 through the field displayed on the screen a Help Text dialogue box 256 opens with the field in question displayed and the full authoritative definition 258 provided. When the dialogue box is closed, the pen stroke through the label is erased.

C. Server Synchronization Phase

In accordance with an embodiment, an enterprise-level Forms Server provides DirectForms™ with centralized process control, managed distribution of form revisions as well as several unique technical features, including:

Work queues and forms routing specific to each form, which allow for sharing of forms between users to ensure that the right person collects the data at the right place and time. Rules-based conditional routing of forms to specific specialists or managers, based on data entered in the form, allows for important workflow steps, including signatures or other management input.

Form-specific data paths that are used to produce HL7 transaction and other industry-standard or proprietary files for each set of patient data.

An HL7 transaction type "unsolicited transmission of an observation message (an HL7 event type ORU-R01) can be included, to conform with clinical reporting standards. Both the patient's Medical Record Number and the Encounter Number (or Visit Number) can be included in the PID segment.

The order record segment can include a code to identify the kind of data captured on the specific form and indicates to the importing system where to store the data.

Discrete observation segments transmit each field value identified by field name. Secure TCP-IP transmission to receiving systems allows HL7-compliant transactions to be sent via point-to-point connection or via a centralized interface engine.

Figure 28:
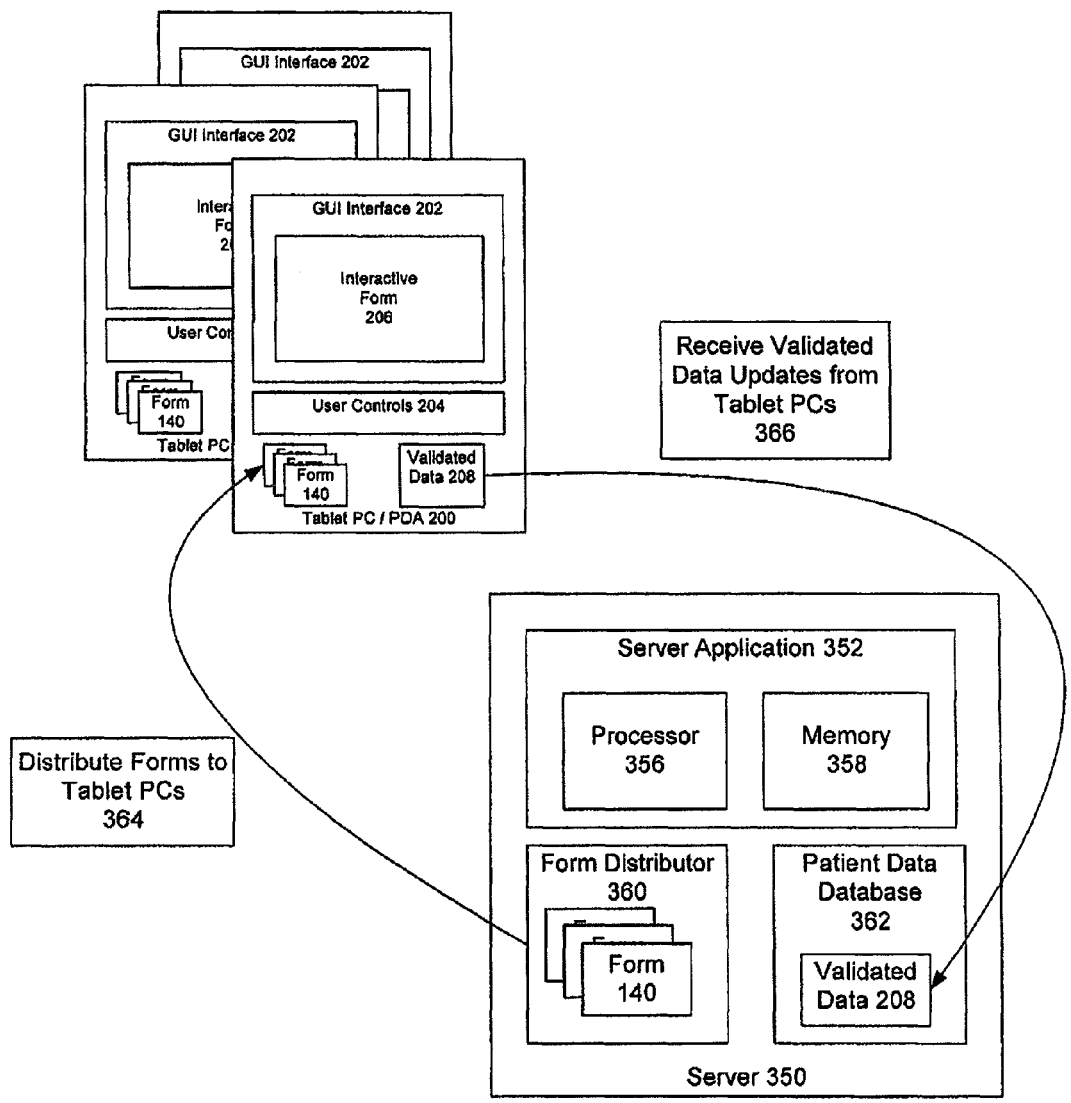
FIG. 28 illustrates the server phase in accordance with an embodiment.

FIG. 28 illustrates the server phase in accordance with an embodiment. As shown in FIG. 28, once the patient data has been collected on one or more tablet PC, it can be communicated to a server for subsequent use. As shown in FIG. 28, the server is initially responsible for distributing forms to the tablet PCs 364. The tablet PCs are then used to collect data as described above. Once the data has been collected, either on demand or at the end of a time period, for example, daily or weekly, then the validated data updates can be communicated from the tablet PC to the server 366. In accordance with an embodiment, the server 350 includes a server application 352 including a processor 356 and memory 358. The server further comprises a form distributor 360, which is responsible for distributing to the tablet PCs. The server further comprises a patient data database 362. As data updates are received from the tablet PCs, the validated data is stored in the patient data database. The server can then use this information, or communicated to a clinical system or external system as described further detail below.

Figure 29:
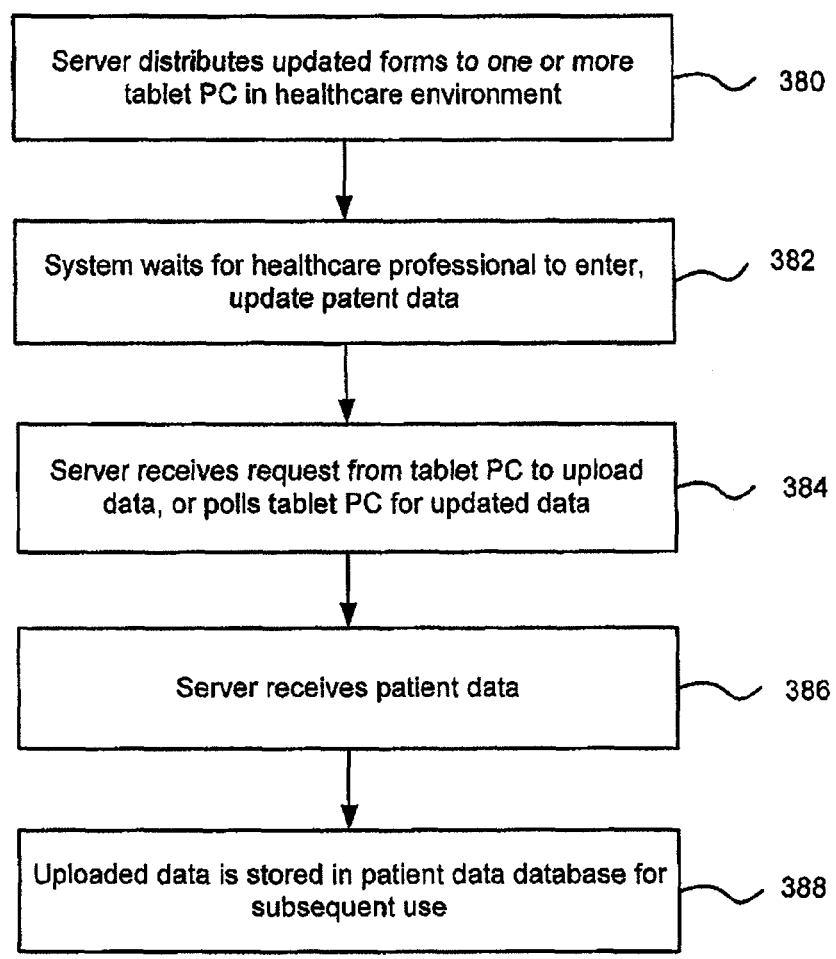
FIG. 29 is a flowchart that illustrates the steps of the server phase in accordance with an embodiment.

FIG. 29 is a flow chart that illustrates the steps of the server phase in accordance with an embodiment. As shown in FIG. 29, in step 380 the server distributes updated forms to one or more tablet PCs in the healthcare environment. The system then waits for a healthcare professional to enter, update or modify the patient data in step 382. In step 384, the server ultimately receives a request from the tablet PC to upload data. Alternatively the server can poll the tablet PC on a regular basis for updated data. Typically this may be every minute, every hour, at the end of a shift, or at the end of a work day. In step 386 the server receives the patient data. In step 388, the uploaded data is stored at the server in a patient data database for subsequent use such as clinical analysis or communication to another system including a registry or clinical database.

It will be evident that these examples illustrate the types of data flows that can be used, and that other examples and types of data flow can be developed or implemented within the spirit and scope of the invention.

D. Clinical Database Phase

In accordance with an embodiment, when validated data on the tablet PC (or a plurality of tablet PCs) is ready, then the process of uploading the data to the server, and the subsequent generation of the HL7 transaction files, or other external data communication, can occur. Within minutes the data can be stored in an enterprise database management system, clinical database, external service, or registry, where reporting and analysis can begin in accordance with the procedures and applications already in place at those enterprise and database systems. Additional features of the clinical database upload component include:

- A sophisticated interface logic that allows one transaction file to be sent to multiple clinical repositories or multiple data modules simultaneously.
- A logic that ensure final validation of critical information, such as patient identifiers, which may have changed recently, and which occurs as part of the interface process.
- Application routines for merging the collected data about a patient with the patient's existing data records in the clinical database, as applicable. This immediately locates the data from the tablet PC into the larger context of the patient's electronic health record and other clinical datasets.

Figure 30:
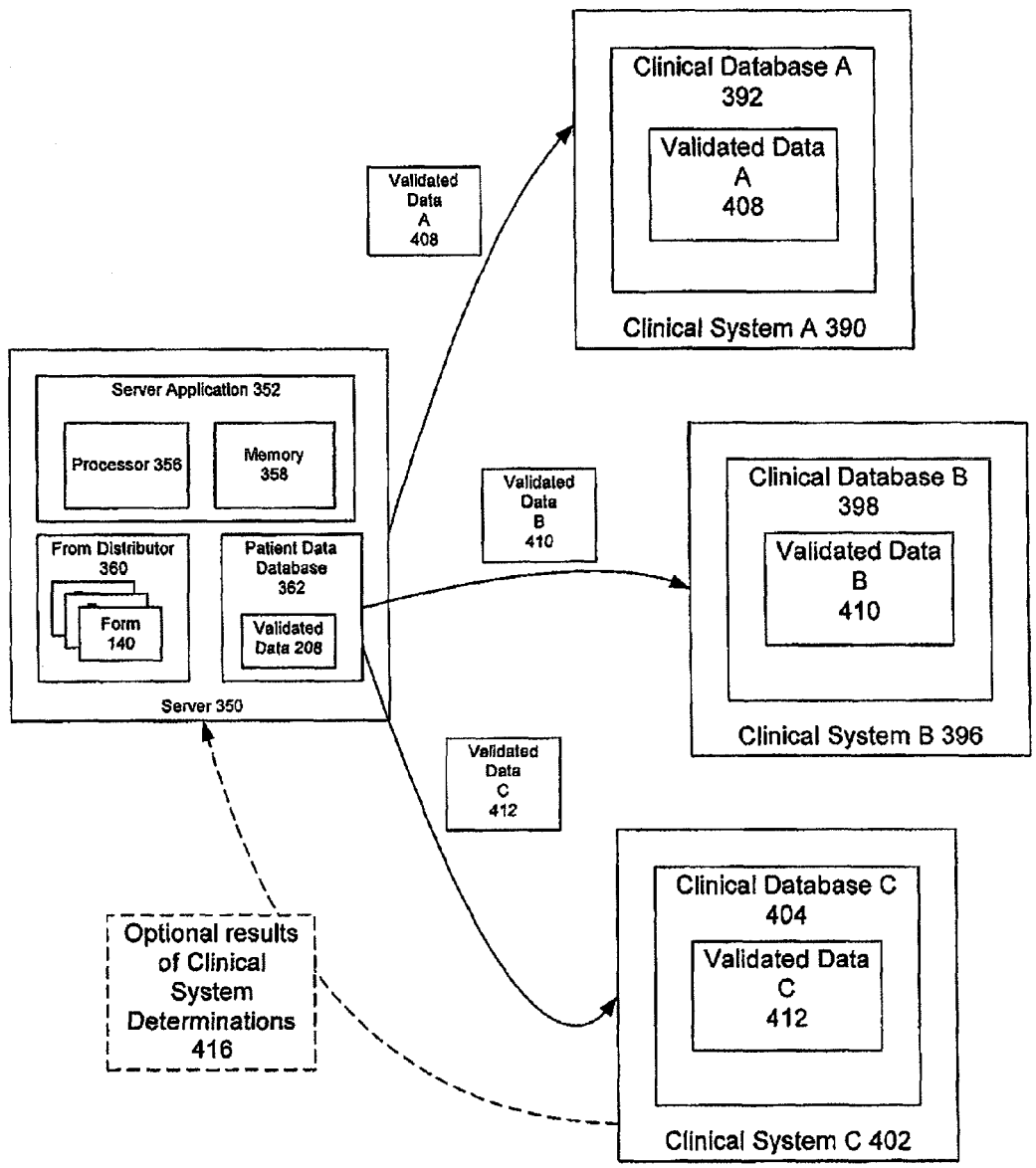
FIG. 30 illustrates the clinical database phase in accordance with an embodiment.

FIG. 30 illustrates the clinical database phase in accordance with an embodiment. As shown in FIG. 30, the server can communicate with any of a variety of clinical database systems, to share information about the patients and communicate information to the clinical database systems. Depending on the particular application, the information may be used by the clinical system to identify patients of particular interest, or to determine course of treatments. As shown in FIG. 30, the server is capable of communicating with a variety of clinical systems including example clinical system A 390, B 396, and C 402. Each of the clinical systems typically includes their own clinical database including A 392, B 398, and C 404. Information including validated patient data (e.g. validated data A 408, validated data B 410, and validated data C 412) can be communicated from this server to each of the clinical databases at the clinical systems. Optionally, results of the clinical systems determinations 416 can be communicated back to the server and used in the healthcare environment for example to identify particular patients or courses of treatment. As shown in FIG. 30 each of the clinical databases may have particular needs, for example cardiology related applications, or post operative patient tracking system. It will be evident that other clinical applications can be included in accordance with other embodiments.

Figure 31:
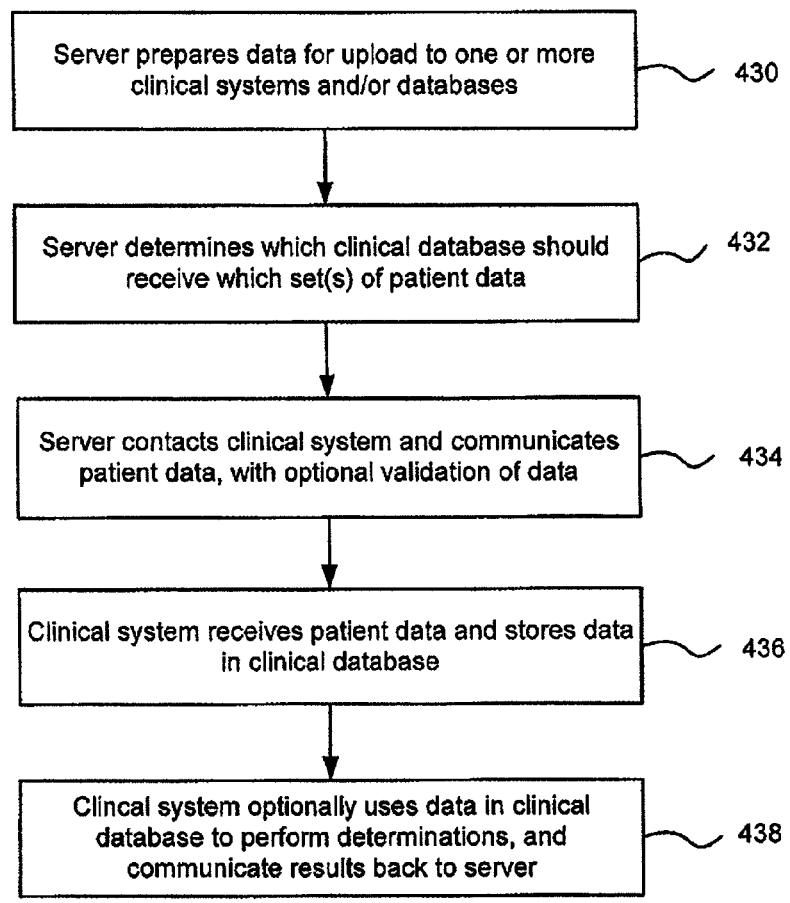
FIG. 31 is a flowchart that illustrates the steps of a clinical database phase in accordance with an embodiment.

FIG. 31 is a flow chart that illustrates the steps of the clinical database phase in accordance with an embodiment. As shown in FIG. 31, in step 430, the server prepares the data for upload to one or more clinical systems or clinical databases. As described above, each of the clinical systems may be specific to a particular need for example cardiological analysis and/or patient tracking. In step 432, the server determines which clinical database should receive which set of patient data. In step 434, the server contacts the clinical system and communicates the patient data to that system. Optionally, the server can validate the data that it is sending to the clinical system, in accordance with any guidelines or rules set down by that clinical system. In step 436, the clinical system receives the patient data and stores the data in its clinical database. The data may then be used by the clinical system for any of a number of reasons including for example determining particular patients or courses of treatment. In step 438, the clinical system can optionally use the data to perform determinations and communicate those results back to the server, which will ultimately be used in the healthcare environment by professionals to determine patient treatment and other day-to-day function of the healthcare environment.

It will be evident that these examples illustrate the types of data communication that can be used between the server and one or more clinical databases, and that other examples and types of clinical database and server database communication can be developed or implemented within the spirit and scope of the invention.

E. Data Export Phase

In accordance with an embodiment, to transmit the collected clinical data to governmental agencies, payors, or accrediting bodies seeking all or portions of the data, the system uses export tools specific to each data harvest to extract, format and package the collected data. Additional features include:

- Registry-specific file specifications are integrated into a harvest tool at the server, so that file generation, whether quarterly or more frequently, is standardized and automated.
- The use of audit trails and export flags within the local clinical database allows data managers to determine whether records have been harvested for external agencies.

The HL7 data format is a worldwide standard data exchange protocol for exchanging information between clinical applications. This data exchange protocol defines the format and the content of the messages that applications use to exchange data in various circumstances. In accordance with an embodiment the system uses a dedicated logic to create HL7 message files for transmission of data collected on tablet PCs to any clinical application in the healthcare enterprise. Data acquired from the tablet PCs by the forms server is stored after all forms routing has been completed. An HL7 export utility then maps the newly acquired data to a standard HL7 transaction and places it in a queue for transmission to the clinical database application.

Figure 32:
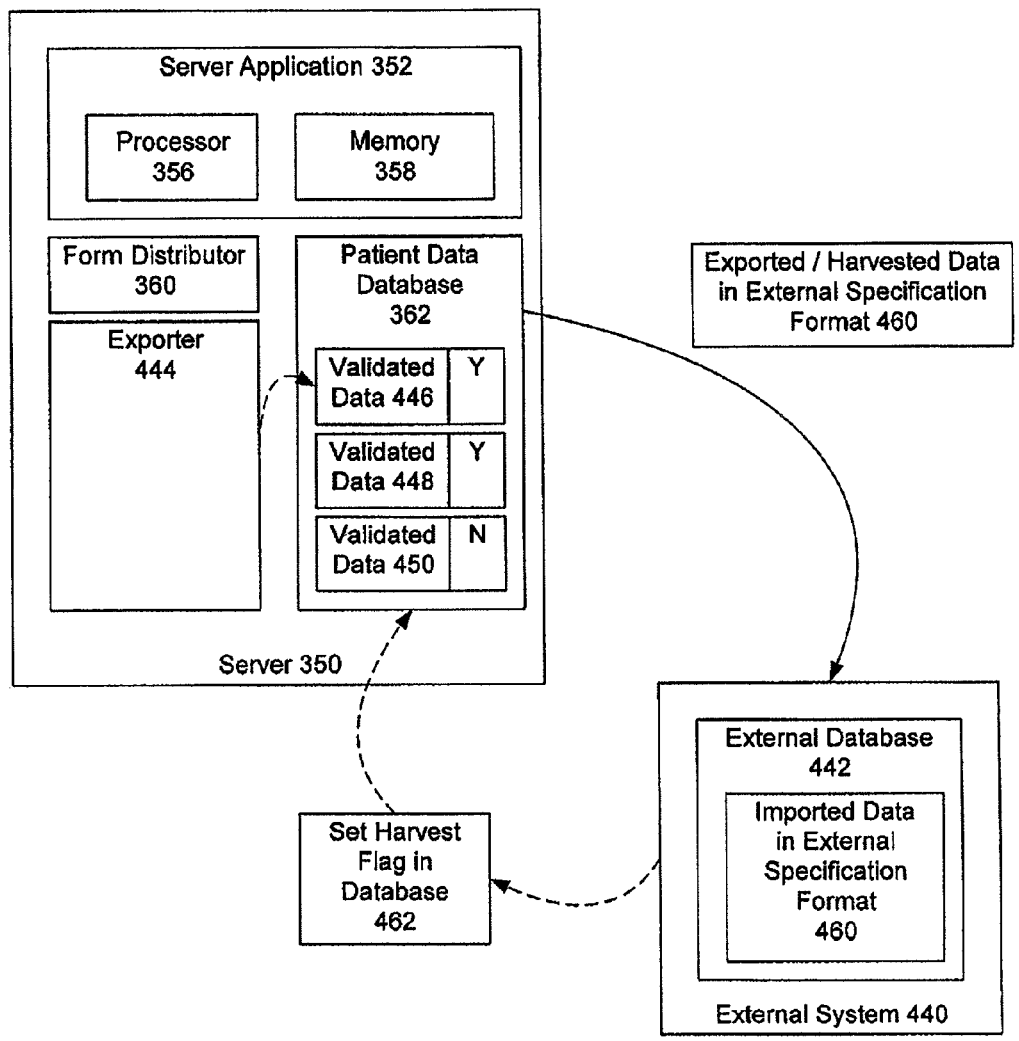
FIG. 32 illustrates the data export phase in accordance with an embodiment.

FIG. 32 illustrates the data export phase in accordance with an embodiment. As shown in FIG. 32, the server can communicate information to external databases including converting the information to formats needed by those external databases when necessary. In accordance with an embodiment, as shown in FIG. 32, the server includes an exporter function 444 whose responsibility is to export portions of the validated data in the patient data database (e.g. validated data 446, validated data 448, and validated data 450) to external systems. As shown in FIG. 32, the external system 440 includes a database 442. When the information is exported or harvested for the external system, it is communicated in the format required by the external system 460 and used to populate the database. At the same time a harvest flag is set by the exporter or harvest utility in the database 462 indicating that the information has been communicated to or harvested for the external system.

Figure 33:
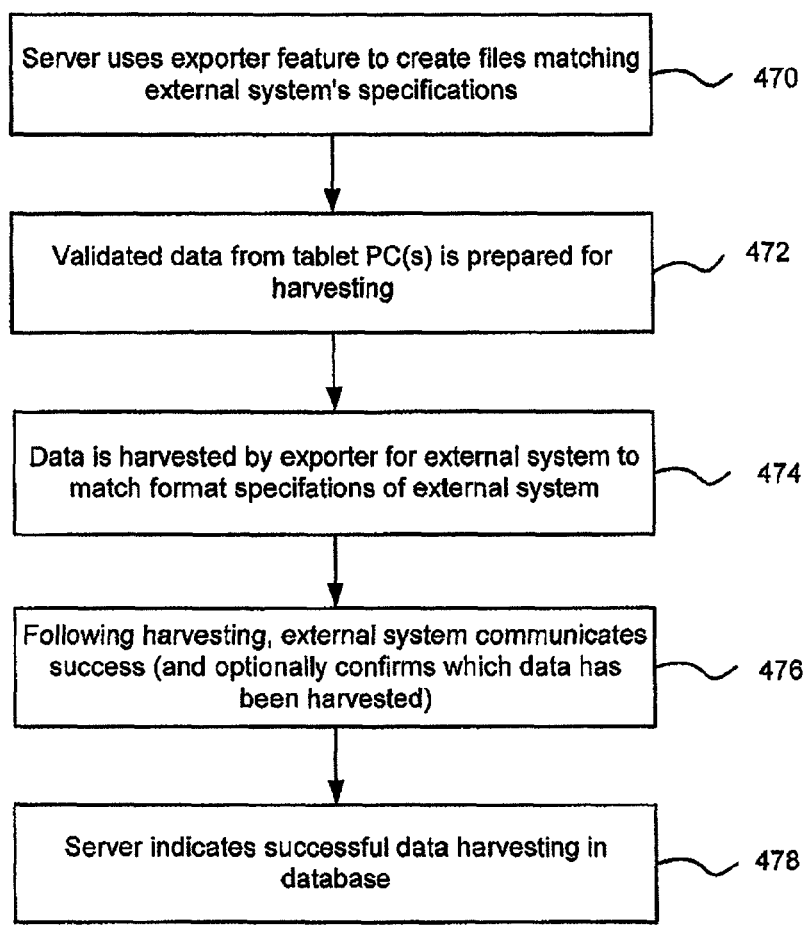
FIG. 33 is a flowchart that illustrates the steps of the data export phase in accordance with an embodiment.

FIG. 33 is a flow chart that illustrates the steps of the data export phase in accordance with an embodiment. As shown in FIG. 33, in step 470, the server uses an exporter feature to create files matching the specification of the external system. In step 472 data is communicated from the tablet PCs and prepared for harvesting for the external system. In step 474, data is harvested to match the format specifications of the external system. In step 476, following harvesting the external system communicates success in receiving the data. In step 478, the server then indicates by flags or other means which data in its database has been harvested.

FIG. 34 illustrates a message base export in accordance with an embodiment. As shown in FIG. 34, the technique of sending an export message comprises four steps including a first step 492 of acquiring data from the form server session storage. A message template is then used to map data fields to a HL7 message format in step 494. The message is created 496 by parsing the data into a transaction file. Finally, the message is communicated 498 by transmitting the transaction file to the other systems.

FIG. 35 illustrates a HL7 message export in accordance with an embodiment. As shown in FIG. 35, the file layout 510 includes a plurality of lines including a number of delimited fields, for example, patient identifiers and courses of treatment.

Forms-Based Data Collection for National Registries

Figure 36A:
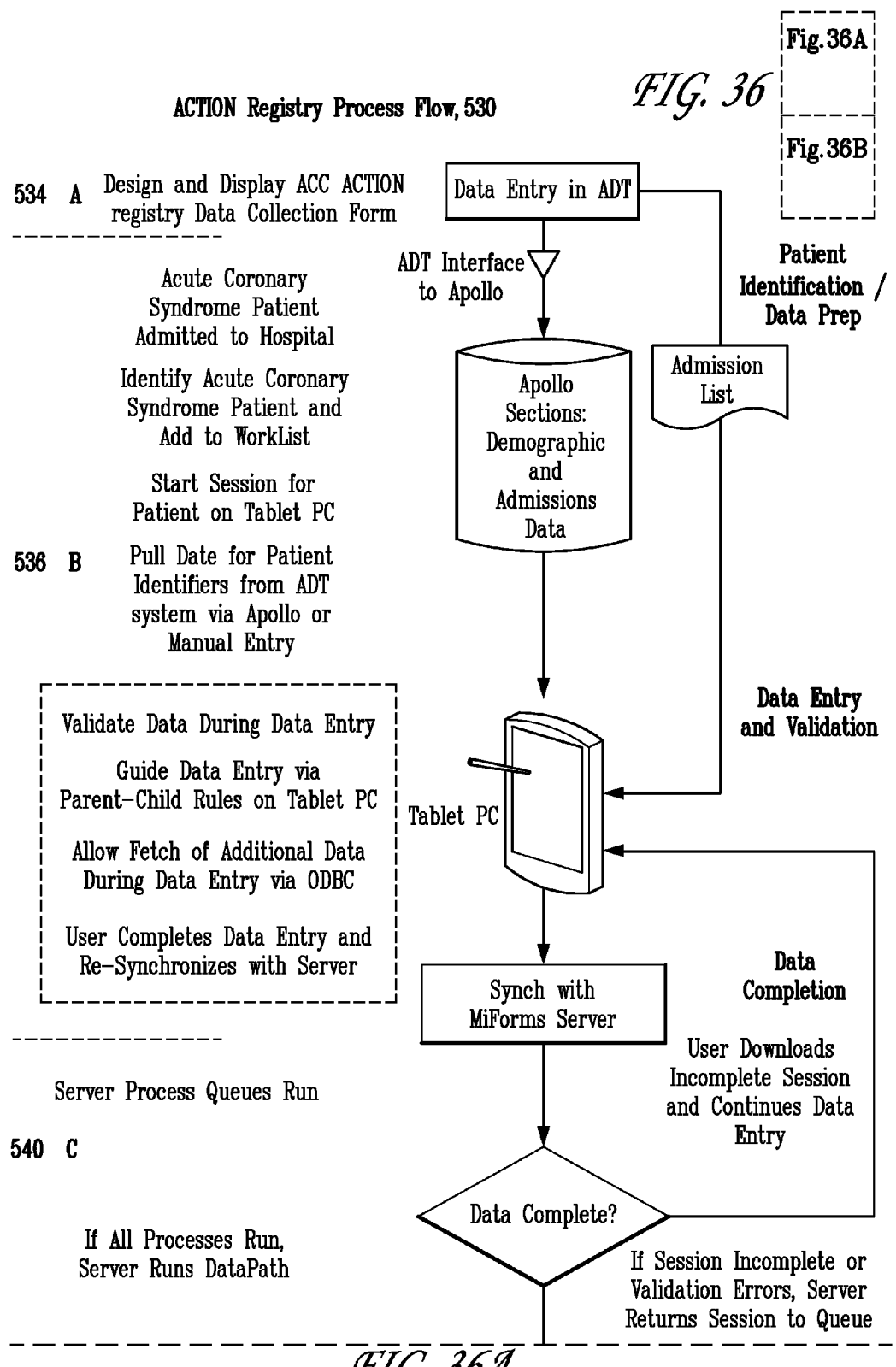
FIG. 36 illustrates how the phases of providing healthcare data collection and management using a portable device can be applied to an ACTION Registry in accordance with an embodiment.

FIG. 36 illustrates how the phases of providing healthcare data collection and management using a portable device are applied in a nationwide ACC-NCDR ACTION clinical registry. As shown in FIG. 36, each of the steps A 534, B 536, C 540, D 544 and E 550 can be used to design forms specific to the ACTION registry, deploy those forms on tablet PCs, receive the data input to a server, and communicate that data to another server or entity, for example to an external registry, in a format that can be understood by that receiving registry. The format may include for example HL7, or another universal format, or an entity-proprietary format.

The first step of the process in creating an application or registry specific form is the identification of a specific data collection need, and clarification of the data definitions involved. As shown in FIG. 36, these needs and data definitions can be matched to those of the ACTION registry. In accordance with an embodiment, a healthcare institution purchases tablet PCs that can authenticate on the institution's network domain and that are then loaded with the forms, or a forms client. Depending on the particular embodiment, the system can be customized for the particular healthcare professional that will be using the form (i.e., a surgeon in middle of a case may not be able to use a tablet PC, but the circulating nurse or data specialists could, so the forms can be tailored for their needs).

Once the particular needs and definitions of the registry have been ascertained, (in this example the ACTION registry), and the users who will use the forms have been identified, then the DirectForms™ process, including the phases described above, can be employed to collect the patient data, and communicate it to the clinical database or registries as needed.

Data Collection and Upload Dataflow Models

Depending on the particular embodiment, the dataflow model employed in the DirectForms™ process can be unidirectional or bidirectional. When used with a national registry the main focus is on ready capture of patient data close to the point of care, so the main direction is unidirectional, e.g., from the tablet PC to a clinical database, and from there to a national registry. FIGS. 37-40 illustrate different data flow models in accordance with various embodiments.

Acute Care Dataflow Model

Figures 37, 38, 40:
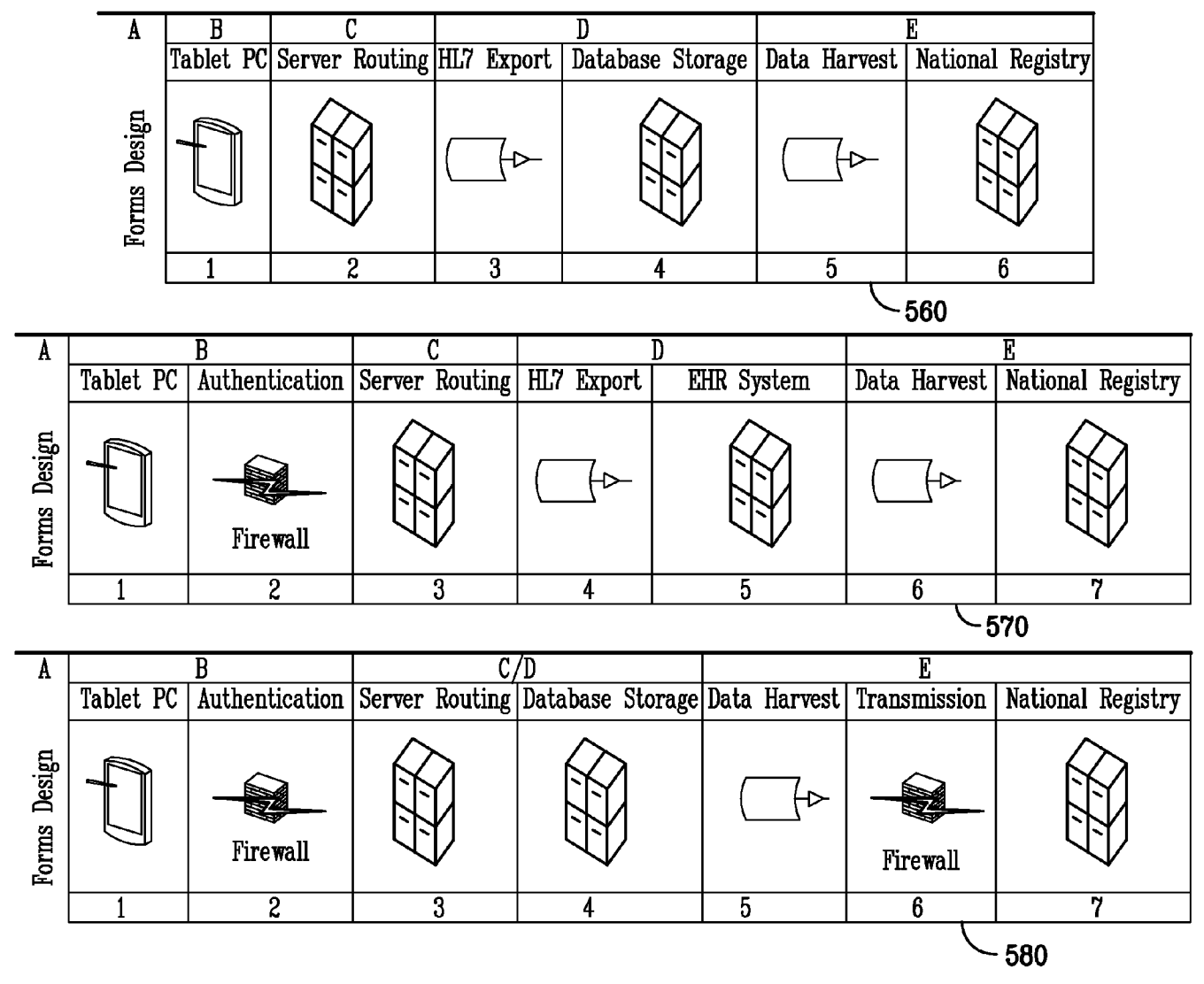

FIG. 37 illustrates an Acute Care Dataflow Model 560 in accordance with an embodiment. As illustrated in FIG. 37, in this dataflow model the tablet PCs are used at the point of care (stage 1), at the patient bedside, or in the operating room, or in another clinical location. The supporting infrastructure, (illustrated in stages 2-5), including the forms server, export utility, clinical database and harvest utility) are all located in the hospital or enterprise datacenter.

The acute care model is distinctive from the standpoint of data security. The tablet PCs, servers and clinical database are all contained within the enterprise network. Only after the data is harvested (stage 5) is there an opportunity for the data to be read by an outside entity. This closed dataflow model is designed to fit Health Insurance Portability and Accountability Act (HIPAA) data privacy rules governing the collection and storage of patient data in a hospital setting.

Ambulatory Care Dataflow Model

Figure 39:
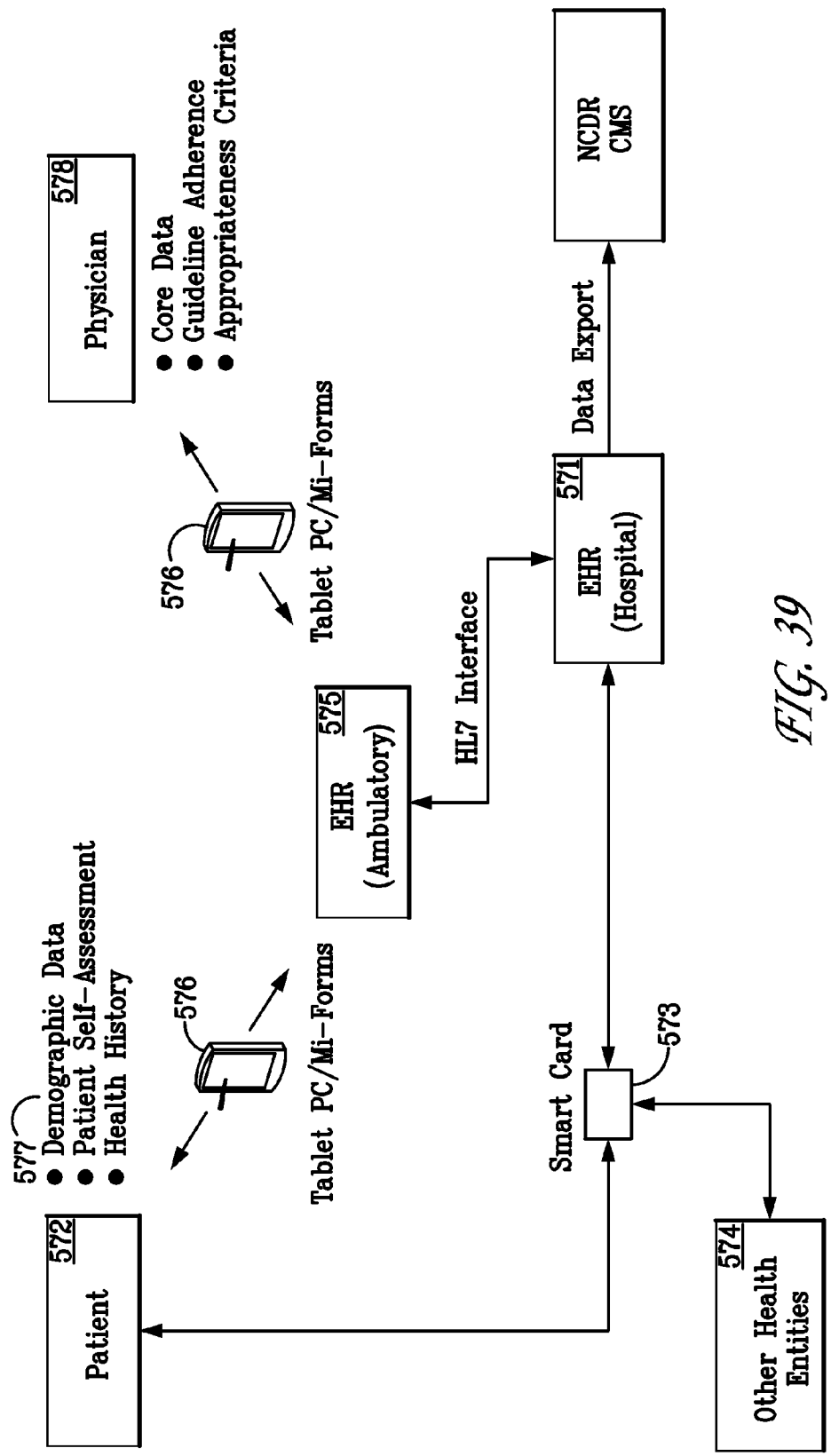
FIG. 39 illustrates the participants in an ambulatory data flow model in accordance with an embodiment.

FIG. 38 illustrates an Ambulatory Care Dataflow Model 570 in accordance with an embodiment. As illustrated in FIG. 38, collecting data on patients in a clinical setting outside of the hospital is difficult. In a physician-based ambulatory care dataflow model, tablet PCs are used in the physician offices to provide efficient data capture. FIG. 39 illustrates the participants in an ambulatory data flow model in accordance with an embodiment. As illustrated in FIG. 39, a hospital or other healthcare facility can maintains an electronic health record (EHR) 571 for a group of patients. If a particular patient 572 is issued with a smart card 573 or other identification material, then data about that patient can be communicated to and from the local EHR and other health entities 574. In some instances the information can be communicated directly, such as during in-patient treatments. However, the ambulatory care dataflow also allows information to be communicated through an ambulatory care EHR 575. The ambulatory care EHR communicates forms, and other information to the tablet PCs 576, which in turn are used by a patient either for self-assessment 577, or by a physician or health care professional interacting with the patient in a physician office setting 578. Data can then be communicated back to the ambulatory EHR, and from there to the hospital EHR, using HL7 or another means. Since the cost of implementing the system might otherwise be expensive for smaller physician practices, and since there is interest in connecting referring physicians to the local hospital's EHR, the ambulatory care dataflow model allows the tablet PCs to be used in the physician office, while the forms are stored separately, for example at the hospital site. The tablet PC's then access the Forms server remotely, authenticating the identity of the user at the hospital's firewall (stage 2) and interfacing the data to the EHR (stage 4).

One of the advantages of this model is it extends the use of the DirectForms™ process into the office of the physician, allowing data collection for comprehensive disease management. Healthcare institutions are generally prohibited from providing computers to private physicians, so the use of tablet PC-based data collection forms allows the data collection process to be automated while requiring a method of Internet access to transfer forms, and completed electronic form data.

The concerns for satisfying HIPAA standards can be met by encrypting the data on the tablet PCs, and then completely removing the data when the tablet docks with the server. For example, in accordance with an embodiment, a Heart Failure Project can be employed using the ambulatory care dataflow model. In this embodiment, tablet PCs taken to the patient's home by visiting nurses allow for data collection and validation during the visit, storing the data for later forwarding to the database at the local hospital via an Internet connection. For purposes of research and practice improvement, physician-specific objectives can also be achieved using this data flow model, including for example: Disease Tracking data collection; Disease modality (e.g., Diabetes management); JCAHO Core Measures; Clinical studies; Clinical Guideline Adherence data collection; and Appropriateness of Care Criteria data collection.

Remote Host Dataflow Model

FIG. 40 illustrates a Remote Host Dataflow Model 580 in accordance with an embodiment. As illustrated in FIG. 40, this model allow the tablet PC users to connect with the forms server from anywhere in the nation. The remote host dataflow model locates the Forms server (stage 3) at a hosted service provider, allowing the tablet PCs to connect using a standard Internet connection. When the user is ready to transmit the collected data, the tablet connects with the Forms server (remote host), and is authenticated at the firewall and again at the Forms server.

In the remote host dataflow model, the server pulls the encrypted form sessions from the tablet PC, routes the forms as needed, and stores the data locally. Completed data can be forwarded to national registries or government agencies or insurance payors via a harvest and transmission process.

To simplify management of the process for the hosted service provider, the forms server can store the completed patient data in tables in its own database, consolidating the forms database and the clinical database into one (stage 3 and stage 4). This host can be located at the offices of the national registry, and thereby the harvesting process can be reduced or eliminated.

Participation in the national registries normally requires the purchase of database product specifically designed for the collection and harvesting of the data. A remote host model allows registry data collection almost anywhere in the nation, and also allows transmission to the registry by docking with the server located some distance away, perhaps even on the other side of the country.

Advantages of the remote host dataflow model include lower cost of participation in national registries for healthcare institutions; Fewer steps involved in data collection and submission; Simplified distribution of revised data collection tools; and Simultaneous data collection for multiple registries would be possible through careful design of the data collection forms and storage of the data in multiple tables at the hosted service provider's database.

In accordance with some embodiments, although the forms server may be remote from the tablet PC, the collection and validation of the data may occur at the tablet PC itself. That data can subsequently be communicated to the remote server using the Internet or another communications means. In accordance with other embodiments, the forms server can be provided as an application service provider (ASP), wherein the tablet PC maintains a connection to the remote server, and utilizes the connection and the services provided by the remote server to send data to the server as it is being collected, and to allow the server to perform the validation and additional features offered by that server.

Use of Forms Server with EHR Systems

Figure 41:
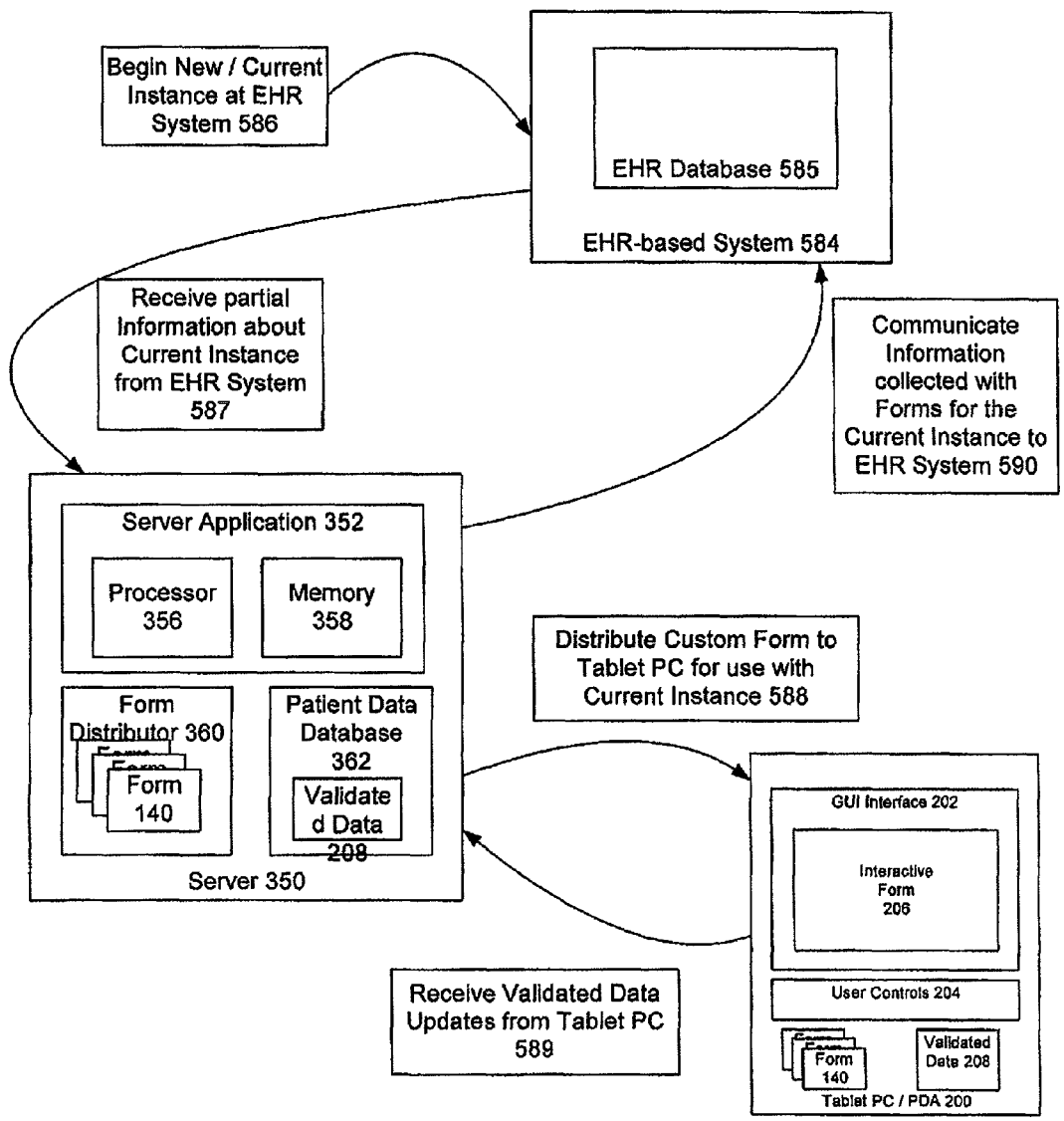
FIG. 41 illustrates an embodiment of the system that uses or provides information to an EHR system.

FIG. 41 illustrates an embodiment of the system that uses or provides information to an EHR system. As shown in FIG. 41, the forms server can be used together with a tablet PC and a hospital's EHR 584, or another form of patient records system, to provide a more accurate data collection process, and to subsequently improve on the overall accuracy of the data stored in the EHR. Within a hospital or healthcare setting the EHR typically includes a database 585 or other storage of patient and patient-related data, including information related to the patient's medical history, past treatments, insurance information, billing, and current course of treatment, including orders, test results, images, analyses and physician reports. The information in the EHR is expected to be completely up-to-date at all times, or at least to the best of the hospital's ability. In accordance with an embodiment, forms can be generated or distributed by the server for a particular patient instance that are largely based on the current information stored in the EHR for that patient. The forms are geared toward collecting the information that is most currently needed by the EHR to create a more complete patient record or to complete an order for a procedure. When the forms are completed on the tablet PC, the information can then be received back into the EHR and used to update the patient record. As shown in FIG. 41, the process may begin 586, for example, with a new patient being admitted to a hospital, or with an existing patient being referred to a new course of treatment, or in the case of an ambulatory EHR with a patient visiting a physician office. The forms server, in combination with the EHR can determine how much additional information is needed to complete the patient data in this instance, perhaps for the proposed course of treatment. This information can be communicated 587 to the forms server. The forms server then determines which forms will be necessary to collect the required information, and then creates or distributes the appropriate form 588 to the tablet PC. In some instances, a complete set of forms can be distributed; in other instances the forms may include only those portions which are relevant to collecting the necessary data. This allows the system to create customized forms for individual patient instances, and reduces the overhead of collecting redundant and potentially inconsistent data. As the forms are completed, validated data is received 589 back to the server. The data is then communicated to the EHR 590 to complete the patient profile and provide the information that the EHR needs in this particular instance.

Figure 42:
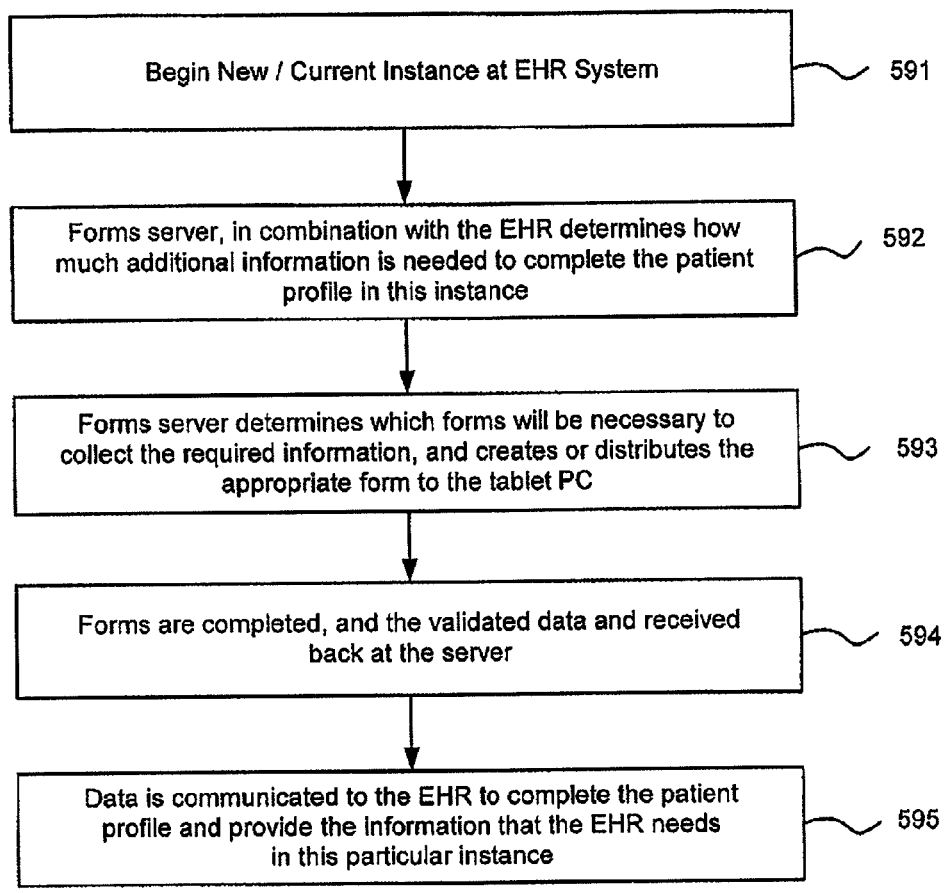
FIG. 42 is a flowchart that illustrates the steps of an embodiment of the system that uses or provides information to an EHR system.

FIG. 42 is a flowchart that illustrates the steps of an embodiment of the system that uses or provides information to an EHR system. As shown in FIG. 42, in step 591 the process begins for example, with a new patient being admitted to a hospital, or with an existing patient seeking a new course of treatment. In step 592, the forms server, in combination with the EHR can determine how much additional information is needed to complete the patient profile in this instance. In step 593, the forms server then determines which forms will be necessary to collect the required information, and then creates or distributes the appropriate form to the tablet PC. In step 594, the forms are completed, and the data is validated data and received back at the server. In step 595, the data is then communicated to the EHR to complete the patient profile and provide the information that the EHR needs in this particular instance.

Clinical Example with Forms-Based Data Collection

The above system and process can be implemented in a wide variety of clinical applications. Of particular importance is the use of the system in cardiac-related clinical applications, so that implementation is described and discussed further herein. It will be evident that other implementations, and other clinical applications, can be deployed within the spirit and scope of the invention.

Patients presenting to hospitals with acute myocardial infarction (AMI) and acute coronary syndrome (ACS) receive attention from organizations assessing the quality of cardiac care. Parameters for the treatment of AMI patients comprise part of the Core Measure data that is required by the Joint Commission on the Accreditation of Healthcare Organizations (JCAHO) as well as other national registries, such as the ACC and the Society of Thoracic Surgeons (STS), which also collect information on AMI and ACS patients who enter the catheterization laboratory or require cardiac surgery. There is considerable overlap in all of these datasets. A dilemma facing nearly all hospitals is finding a cost-effective and accurate way to collect data on ACS and AMI patients, collect data that meets JCAHO Core Measure requirements, collect data that meets STS or ACC requirements, and provide a reasonably complete data source for benchmarking that can be used in quality improvement efforts directed at these patients. In many hospitals, Quality Departments handle JCAHO AMI Core Measures, and they have a variety of vendors available to submit this information to JCAHO. If the hospital participates in other registries, then other more advanced coders, including nurses, may be involved in this more extensive data collection, some of which duplicates or diverges from what has already been done for JCAHO and is also redundant with data elements collected for ACC and STS. In a typical hospital, it is possible that the same or nearly equivalent piece of data may be independently collected 5 or more times during and after an ACS or AMI admission. Although the data for JCAHO is easier and less time consuming to collect and enter, many clinicians believe that the data collected for these efforts is too minimal and is not useful in understanding differences in outcomes or providing direction for quality improvement efforts. As a result, many hospitals that continue to collect all of this data to meet the demands of all these users are buckling under the weight of the data collection effort.

In accordance with an embodiment, the system can be implemented to collect data on AMI and ACS patients using the Tablet PC/Forms system, and to provide direct transmission of that data. For example, the ACTION registry is currently operated by the ACC-NCDR with the data management and reporting operated through the Duke Clinical Research Institute (DCRI). In accordance with one embodiment, the system includes the following features:

Use of the Tablet PC/Forms system within a hospital system to collect ACTION data from multiple institutions that are interfaced to a local cardiac database, and transmit this to DCRI via a data harvest file.

Processing and feedback mechanisms at DCRI to interact with hospitals that submit their ACTION data via this Tablet PC/Forms approach.

As described above, one advantage of this software is that a form can be built and deployed with automatic validation and consistency checks for ACTION data similar to what might be found in the ACC's own web-based data entry tool. As also described above, the forms software provides powerful capabilities for "pre-filling" forms with data from other local databases and the capability to export data in standard HL7 format that can be read by almost all medical software packages.

Models developed in accordance with these steps can then be used at additional hospitals to allow them to also participate in the ACTION national registry.

Figure 43:
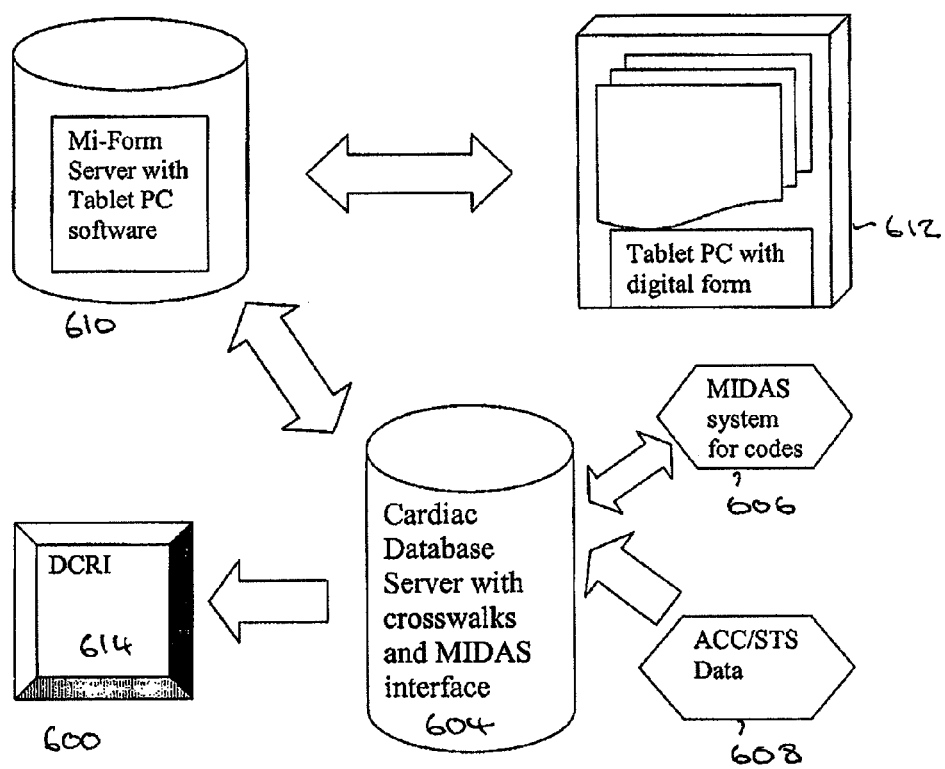
FIG. 43 illustrates a Cardiac Database implementation in accordance with an embodiment.

FIG. 43 illustrates a Cardiac Database implementation 600 in accordance with an embodiment. As shown in FIG. 43, the system comprises a cardiac database server with an interface to a clinical quality management system (for example, MIDAS) 604, including interfaces for clinical procedure codes 606 and ACC/STS data 608. The system further comprises forms 610 that can be loaded and completed on a tablet PC 612. Information about patients can be entered and submitted to the Duke Clinical Research Institute (DCRI) 614. In typical usage:

1) patients are identified through the clinical database system, or through bedside observation;
2) a list or automated query is created which is then used to query the local clinical database. Data that exists from the demographic, cardiac catheterization or cardiac surgery modules are prepared for transfer to the Tablet PC/Forms system;
3) data sets are then downloaded from the relevant modules to pre-fill the ACTION form implemented on the Tablet-PC/Forms system;
4) data are collected by the healthcare professional and validated on the tablet PC;
5) a data export in HL7 format is created and transferred back to the cardiac database;
6) an export file is created for transmission to the external registry (for example, DCRI) as well as an AMI Core Measures file to the JCAHO Core Measure reporting system.

Studies show that implementation of the system described above may result in a significant decrease in the amount of time required to process patients for the ACTION registry. In addition, when the ACTION form is preloaded with information already residing in the local cardiac database at the hospital or healthcare institution, further significant reductions in time are achieved. Studies also indicate that the Tablet PC/Forms system is significantly more efficient and accurate compared to the current paper or web-based systems for collecting ACTION registry data. In addition, the Tablet PC/Forms based approach is particularly suited to reusing or merging contemporaneous patient data with data already existent in a local cardiac database, further enhancing the data collection process.

Figure 45:
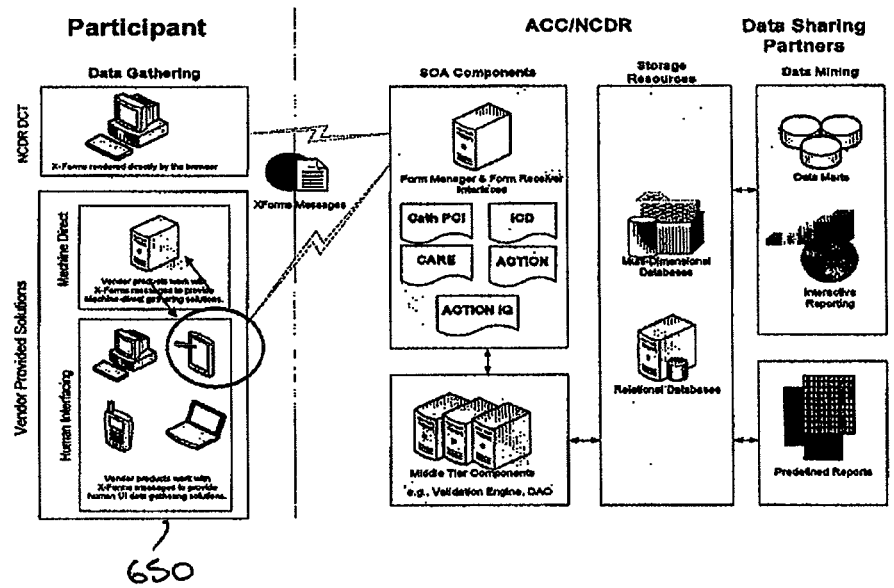
FIG. 45 illustrates a Cardiac Database real-time business framework in accordance with an embodiment.

In this manner a registry such as the ACC-NCDR can use flexible Tablet PC/Forms for collecting clinical data for all of the current national registries. FIG. 44 illustrates a variety of Cardiac Database registries 630 in accordance with an embodiment. Although NCDR currently works with certified database software vendors, little attention has been paid by the software vendors to streamlined ways to enter and validate data. There are also a number of institutions that would like to participate in one of the NCDR national registries, but lack the resources to maintain a local database system. FIG. 45 illustrates a cardiac data collection real time business framework 650 in accordance with an embodiment that can address these issues. The Forms/Tablet PC architecture as developed for use with the ACTION registry can be used in a similar manner to support the many hospitals participating in these national registries, and can be used to gather data for any of the several ACC-NCDR data registries via rapid, flexible form design and deployment.

Additional System Enhancements

Embodiments of the DirectForms™ system and process may also include features such as:

A version of the data collection process that can either be used with interfaces to local clinical databases or used independently with a direct connection to a registry's or government agency's data via an Application Hosting model.

Elements of an expert system, to calculate risk and to perhaps suggest analysis or maybe even diagnosis/treatment, with caution flags highlighting the data upon which the suggestion is based.

A Web-services-based tool that will allow managers to control workflow, route specific forms to users and a dashboard-like screen where they could track data collection tasks while they are underway and identify the clinician tracking a specific patient.

Integration of Speech Recognition software, especially in narrative input tools designed to capture physician summary reports and care plans.

Reports and analytical tools for benchmarking developed for cardiology and for other disciplines using SQL Server Reporting Services tools.

An improved User Administration tool for login management, tracking user forms history and user productivity.

Appropriate software coding can readily be prepared by skilled programmers based on the teachings of the present disclosure, as will be apparent to those skilled in the software art. The invention may also be implemented by the preparation of application specific integrated circuits or by interconnecting an appropriate network of conventional component circuits, as will be readily apparent to those skilled in the art.

The present invention may include a computer program product which is a storage medium (media) having instructions stored thereon/in which can be used to program a computer to perform any of the processes of the present invention. The storage medium can include, but is not limited to, any type of disk including floppy disks, optical discs, DVD, CD-ROMs, microdrive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data.

Stored on anyone of the computer readable medium (media), the present invention includes software for controlling both the hardware of the general purpose/specialized computer or microprocessor, and for enabling the computer or microprocessor to interact with a human user or other mechanism utilizing the results of the present invention. Such software may include, but is not limited to, device drivers, operating systems, and user applications. Ultimately, such computer readable media further includes software for performing the present invention, as described above.

Included in the programming (software) of the general/specialized computer or microprocessor are software modules for implementing the teachings of the present invention, including, but not limited to capturing and annotating media streams, producing a timeline of significant note-taking events, linking still frames to points in or segments of a media stream, recognize any slide changes, production and distribution of meta data describing at least a part of a media stream, and communication of results according to the processes of the present invention.

The present invention may be conveniently implemented using a conventional general purpose or a specialized digital computer or microprocessor programmed according to the teachings of the present disclosure, as will be apparent to those skilled in the computer art.

The foregoing description of the present invention has been provided for the purposes of illustration and description. It is not intended to be exhaustive or to limit the invention to the precise forms disclosed. Many modifications and variations will be apparent to the practitioner skilled in the art. Particularly, while certain healthcare applications, forms, clinical databases, and registries were described herein, it will be evident that the systems and methods described herein can be used with other applications, healthcare applications, forms, databases, clinical databases, and registries in addition to those described. Additionally, while certain embodiments are described as being implemented with tablet PCs, it will be evident that the systems and methods described herein can be used with other devices, including PDAs, portable computers, handheld devices, and other devices in addition to those described. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A system for recording and providing healthcare data comprising:
   a tablet having an interactive graphical user interface including
   a plurality of interactive forms for use with a healthcare application, wherein one or more forms are configured with rules that enable the tablet via the interactive graphical user interface to guide a user to enter patient data in a directed manner and the tablet validating the patient data during data entry, and storing the patient data for upload to a server,
   the server configured to store and distribute forms to the tablet, synchronize the patient data uploaded from the tablet, and communicate the patient data to a clinical database;
   a server-based software utility configured to prepare and send data to at least one of a clinical system, clinical database, national registry, healthcare payor, and governmental agency; and
   the clinical database in communication with the server, the clinical database configured to host the healthcare application, receive the patient data uploaded from the tablet to the server, and use patient clinical data included in the patient data to make one or more treatment determinations about a patient.

2. The system of claim 1, further comprising:
   a second software utility operating on a computing device and in communication with the server, the second software utility configured to provide for a healthcare institution to retrieve at least a portion of the patient data at the server or the clinical database and format the retrieved portion per one or more specifications.

3. The system of claim 1 wherein at least one form includes one or more navigation tools, the navigation tools including any of tabs, arrows, graphic-linked hotspots, and field-linked programming functionality, the navigation tools allowing the user to jump to a portion of the form on the tablet.

4. The system of claim 1 wherein for at least a portion of one or more forms, specific fields, pages or forms are hidden to reflect that portions of that form need not be completed, and wherein a decision to hide or show the fields or pages is based at least in part on preceding data entry into the form.

5. The system of claim 1 wherein a form includes one or more retrieve and populate pick lists, and wherein data used to populate the pick lists is stored and retrieved from tables on the tablet.

6. The system of claim 1 wherein a form is visually similar to one or more of an ACC-NCDR ACTION national registry Form, ACC-NCDR Cath/PCI national registry Form for collection of cardiac catheterization data, ACC-NCDR ICD national registry Form for collection of implantable cardioverter defibrillator procedure data, ACC-NCDR CARE national registry Form for collection of carotid artery stent procedure data, STS Adult Cardiothoracic Surgery national registry Form for collection of cardiac surgery data, STS General Thoracic national registry Form for collection of thoracic surgery data, or STS Congenital Cardiac Surgery national registry Form for collection of pediatric or congenital cardiac surgery data, JCAHO Acute Myocardial Infarction Core Measures form, JCAHO Heart Failure Core Measures form, and JCAHO Stroke data form.

7. The system of claim 1 wherein a form is designed to collect a set of data that meets the requirements of one or more of an ACC-NCDR ACTION national registry Form, ACC-NCDR Cath/PCI national registry Form for collection of cardiac catheterization data, ACC-NCDR ICD national registry Form for collection of implantable cardioverter defibrillator procedure data, ACC-NCDR CARE national registry Form for collection of carotid artery stent procedure data, STS Adult Cardiothoracic Surgery national registry Form for collection of cardiac surgery data, STS General Thoracic national registry Form for collection of thoracic surgery data, STS Congenital Cardiac Surgery national registry Form for collection of pediatric or congenital cardiac surgery data, JCAHO Acute Myocardial Infarction Core Measures form, JCAHO Heart Failure Core Measures form, and JCAHO Stroke data form.

8. The system of claim 1 wherein a form is any of a multi-day surgery patient tracking form and a multi-day cardiac rehabilitation patient tracking form.

9. The system of claim 1 wherein the server distributes one or more updated copies of one or more forms to the tablet.

10. The system of claim 1 wherein the system includes a plurality of computing devices and wherein the server distributes one or more updated copies of one or more forms to the plurality of computing devices.

11. The system of claim 10 wherein a form includes one or more attached picklist files.

12. The system of claim 10 wherein data collected from a first computing device is used to modify the distribution of one or more forms displayed on a second computing device.

13. The system of claim 1 wherein the server further validates the patient data.

14. The system of claim 1 wherein the server is configured to communicate information to the clinical database in an HL7 format.

15. The system of claim 1 wherein the system comprises a plurality of clinical databases, and wherein the server can choose which clinical databases should receive which patient data.

16. The system of claim 1 wherein the clinical database merges the patient data received from the server with existing information for the patient associated with the received patient data.

17. The system of claim 1 wherein an external database receives at least a portion of patient data created by a healthcare institution using a utility designed to select portions of patient data from the server in a format specified by the external database, and once the data is harvested then setting a flag in the server indicating the data has been received.

18. The system of claim 1 wherein the tablet is used at a point of care in a health care facility.

19. The system of claim 18, wherein any of the server, clinical database and server-based software utility is located at a remote datacenter.

20. The system of claim 1, wherein the tablet is used at a health care facility and the server is operated at a remote location and is accessible to the tablet.

* * * * *